(12) United States Patent
Schäfer et al.

(10) Patent No.: US 6,509,400 B2
(45) Date of Patent: Jan. 21, 2003

(54) TRISRESORCINYLTRIAZINES

(75) Inventors: Thomas Schäfer, Basel (CH); Thomas Bolle, Efringen-Kirchen (DE); Pascal Hayoz, Hofstetten (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/973,397

(22) Filed: Oct. 9, 2001

(65) Prior Publication Data
US 2002/0086922 A1 Jul. 4, 2002

Related U.S. Application Data

(62) Division of application No. 09/303,579, filed on May 3, 1999, now Pat. No. 6,346,619.

(30) Foreign Application Priority Data

May 7, 1998 (CH) ................................. 1036/98

(51) Int. Cl.$^7$ ............................................ C08K 5/3492
(52) U.S. Cl. ................... 524/100; 524/84; 106/164.3; 252/403; 430/512; 544/216
(58) Field of Search ..................... 544/216; 524/84, 524/100; 106/164.3; 430/512; 252/403

(56) References Cited

U.S. PATENT DOCUMENTS

| | | | | |
|---|---|---|---|---|
| 3,118,887 A | * | 1/1964 | Hardy et al. | 544/216 |
| 3,244,708 A | | 4/1966 | Duennenberger et al. | 260/248 |
| 3,249,608 A | | 5/1966 | Biland et al. | 260/248 |
| 3,843,371 A | | 10/1974 | Piller et al. | 96/84 |
| 4,826,978 A | | 5/1989 | Migdal et al. | 544/216 |
| 5,300,414 A | | 4/1994 | Leppard et al. | 430/507 |
| 5,364,749 A | | 11/1994 | Leppard et al. | 430/507 |
| 5,489,503 A | | 2/1996 | Toan | 430/507 |
| 5,556,973 A | * | 9/1996 | Stevenson et al. | 544/216 |
| 5,942,564 A | | 8/1999 | Kaschig et al. | 524/100 |
| 5,962,452 A | * | 10/1999 | Haase et al. | 544/216 |
| 6,111,103 A | | 8/2000 | Ehlis et al. | 544/219 |
| 6,117,997 A | * | 9/2000 | Bulliard et al. | 544/216 |
| 6,184,375 B1 | * | 2/2001 | Huglin et al. | 544/216 |

FOREIGN PATENT DOCUMENTS

| | | |
|---|---|---|
| EP | 0434608 | 6/1991 |
| EP | 0878469 | 11/1998 |
| GB | 2312210 | 10/1997 |
| GB | 2319523 | 5/1998 |
| WO | 94/18278 | 8/1994 |
| WO | 99/26934 | 6/1999 |

OTHER PUBLICATIONS

Ranby, B. et al—Photodegradation, Photo–oxidation and Photostabilization of Polymers—John Wiley & Sons, N.Y. pp. 362–377, 1975.*
Chem. Abstr. 72:121590n (1970) for CH 484695.
Chem. Abstr. 119:213920n (1993) for EP 530135.

English Abstract for EP 0878469, 11/98.
* cited by examiner

Primary Examiner—Peter Szekely
(74) Attorney, Agent, or Firm—Tyler A. Stevenson

(57) ABSTRACT

Compounds of the formula

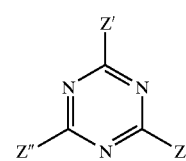
(I)

in which Z, Z' and Z" independently of one another are a group of the formula II

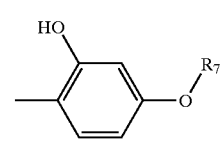
(II)

and $R_7$ is a radical of the formula III, IV or V

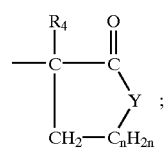
(III)

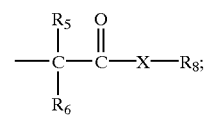

(IV)

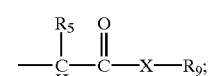

(V)

in which n is 1 or 2; $R_4$, $R_5$ and $R_6$ independently of one another are $C_1$–$C_{18}$alkyl; $C_5$–$C_{12}$cycloalkyl; $C_2$–$C_{18}$alkenyl; phenyl; $C_7$–$C_{11}$phenylalkyl; $C_7$–$C_{11}$alkylphenyl; $C_1$–$C_{18}$alkyl substituted by phenyl, OH, $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, C$_6$–C$_{15}$bicycloalkyl, C$_6$–C$_{16}$bicycloalkyl-alkoxy, C$_6$–C$_{16}$bicycloalkenyl-alkoxy or C$_6$–C$_{15}$tricycloalkoxy; C$_5$–C$_{12}$cycloalkyl substituted by OH, C$_1$–C$_4$alkyl, C$_2$–C$_6$alkenyl or O—COR$_{12}$; or COR$_{15}$; CO—X—R$_{11}$; or SO$_2$—R$_{16}$; or C$_3$–C$_{50}$alkyl interrupted by O and/or substituted by OH, phenoxy or C$_7$–C$_{18}$alkylphenoxy; or $R_5$ and $R_6$ together form a ring structure; X and Y independently of one another are O, NH, NR$_{13}$ or S; and the other symbols are as defined in claim 1 are effective as stabilizers for organic material against the damaging effect of light, oxygen and/or heat.

10 Claims, No Drawings

TRISRESORCINYLTRIAZINES

This is a divisional of application Ser. No. 09/303,579, filed May, 3, 1999, now U.S. Pat. No. 6,346,619.

The invention relates to novel compounds of the 2,4,6-tris(2-hydroxyphenyl)-1,3,5-triazine type, to organic material such as organic polymers or prepolymers stabilized with the aid of these novel compounds, especially coating material, and to the use of these compounds as stabilizers, especially for wood or automobile coatings.

If it is desired to increase the photostability of an organic material such as a coating, it is common to add a light stabilizer. One very frequently employed class of light stabilizers are the UV absorbers, which protect the material by absorbing the damaging radiation by way of chromophores. One important group of UV absorbers is the triphenyltriazines; certain compounds of this type, containing branched ester groups, are described in EP-A-434608, EP-A-530135, U.S. Pat. No. 5,364,749, GB-A-2312210, U.S. Pat. No. 5,489,503 and GB-A-2319523.

For a compound to be an effective stabilizer, not only its spectral and antioxidant properties but also, inter alia, its compatibility with the material to be stabilized and its solubility are of critical importance (see GB-A-2312210).

It has now been found that some compounds of the 2-(2'-hydroxyphenyl)-4,6-diaryl-1,3,5-triazine type which contain specific branched acid or ester side chains do surprisingly have particularly good stabilizer properties and substrate compatibility.

The invention therefore first provides a compound of the formula I

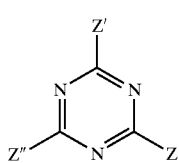

(I)

in which Z, Z' and Z" independently of one another are a group of the formula II

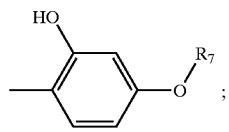

(II)

$R_7$ is a radical of the formula II, IV or V

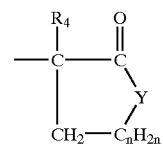

(III)

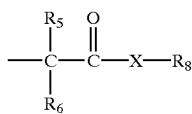

(IV)

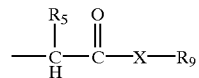

(V)

in which is 1 or 2;

$R_4$, $R_5$ and $R_6$ independently of one another are $C_1$–$C_{18}$alkyl; $C_5$–$C_{12}$cycloalkyl; $C_2$–$C_{18}$alkenyl phenyl; $C_7$–$C_{11}$phenylalkyl; $C_7$–$C_{11}$alkylphenyl; $C_1$–$C_{18}$alkyl substituted by phenyl, OH, halogen; $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkyl-alkoxy $C_6$–$C_{16}$bicycloalkenyl-alkoxy or $C_6$–$C_{15}$tricycloalkoxy; $C_5$–$C_{12}$cycloalkyl substituted by OH, $C_1$–$C_4$alkyl, $C_2$–$C_6$alkenyl or O—COR$_{12}$; or COR$_{15}$; CO—X—R$_8$; or SO$_2$—R$_{16}$; or $C_3$–$C_{50}$alkyl interrupted by O and/or substituted by OH, phenoxy, or $C_7$–$C_{18}$alkylphenoxy; or $R_5$ and $R_6$, together with the carbon atom to which they are attached, form a $C_4$–$C_8$cycloalkyl ring which is uninterrupted or interrupted by O, NH, NR$_{13}$, or S and/or unsubstituted or substituted by $C_1$–$C_6$alkyl, $C_1$–$C_6$alkoxy, OH, phenoxy or $C_7$–$C_{18}$alkylphenoxy;

$R_8$ is H or as defined for $R_{11}$;

$R_9$ is $C_3$–$C_{18}$alkyl; $C_3$–$C_{18}$alkenyl; $C_5$–$C_{12}$cycloalkyl; $C_1$–$C_4$alkylcyclohexyl; $C_6$–$C_{14}$alkyl; $C_7$–$C_{11}$phenylalkyl; $C_7$–$C_{14}$alkylphenyl; $C_6$–$C_{15}$bicycloalkyl; $C_6$–$C_{15}$bicycloalkenyl; $C_6$–$C_{16}$tricycloalkyl or $C_1$–$C_{18}$alkyl substituted by halogen, COOH, COOR$_{11}$, O—COR$_{12}$, CONH$_2$, CONHR$_{13}$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloakyl, $C_6$–$C_{15}$bicycloalkenyl; especially $C_6$–$C_{12}$alkyl;

$R_{11}$ is $C_1$–$C_{18}$alkyl; $C_5$–$C_{12}$cycloalkyl; $C_6$–$C_{14}$aryl; $C_2$–$C_{18}$alkenyl; $C_7$–$C_{14}$alkylphenyl; $C_1$–$C_{18}$alkyl substituted by phenyl, phenoxy, naphthyl, naphthyloxy, OH, halogen, $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkyl-alkoxy, $C_6$–$C_{16}$bicycloalkenyl-alkoxy or $C_6$–$C_{15}$tricycloalkoxy or by a phenyl, phenyloxy or naphthyloxy, which itself is substituted by halogen, OH, $C_1$–$C_4$alkyl, $C_1$–$C_4$alkoxy, $C_1$–$C_8$alkylamino, cyclohexylamino, $C_1$–$C_8$alkylthio, cyclohexylthio; or $R_{11}$ is $C_5$–$C_{12}$cycloalkyl substituted by OH, $C_1$–$C_4$alkyl, $C_2$–$C_6$alkenyl or O—COR$_{12}$; or is COR$_{15}$; CO—X—R$_8$; or SO$_2$—R$_{16}$; or a carbon-linked 5–7 membered heterocyclic residue containing 4–12 carbon and 1–3 heteroatoms selected from O, N and S; or $R_{11}$ is $C_3$–$C_{50}$alkyl interrupted by O, NH, NR$_{13}$, S and/or substituted by OH, phenoxy, $C_3$–$C_{18}$alkenoxy, $C_7$–$C_{18}$alkylphenoxy, O—COR$_{12}$, O—P(=O)(OR$_{12}$)$_2$, O—P(=O)(R$_{12}$)$_2$, O—Si(OR$_{12}$)$_3$;

$R_{12}$ is $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; $C_6$–$C_{15}$bicycloalkyl; $C_6$–$C_{15}$bicycloalkenyl; $C_6$–$C_{15}$tricycloalkyl;

$R_{13}$ and $R_{14}$ independently of one another are $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; or $C_3$–$C_{30}$alkyl interrupted by O, NH or $NR_{13}$ and/or substituted by OH; or are $C_6$–$C_{15}$bicycloalkyl; $C_6$–$C_{15}$bicycloalkenyl; or $C_6$–$C_{15}$tricycloalkyl;

$R_{15}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{16}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{17}$ is $CH_2$—O—$R_{15}$ or furfuryl or tetrahydrofurfuryl or is $C_3$–$C_{30}$alkyl interrupted by O, NH, $NR_{13}$ and/or substituted by OH; and X and Y independently of one another are O, NH, $NR_{13}$ or S, with the exception of the compound 2,4,6-tris(2-hydroxy-4-[1-ethyloxycarbonyl-1-methylethoxy]phenyl)-1,3,5-triazine.

Where two or more radicals bearing the same designation appear within a single compound of the formula I, they may be identical or else different within the scope of the possible definitions indicated. Of particular importance are compounds of the invention in which radicals with the same designation have the same definition.

A halogen substitutent is —F, —Cl, —Br or —I, preferably —F, —Cl or —Br and, in particular, —Cl.

$C_6$–$C_{14}$aryl is generally phenyl, biphenylyl or a corresponding fused carbocyclic aromatic radical; preference is given to phenyl and naphthyl.

Alkylphenyl is alkyl-substituted phenyl; $C_7$–$C_{14}$alkylphenyl embraces examples such as methylphenyl (tolyl), dimethylphenyl (xylyl), trimethylphenyl (mesityl), ethylphenyl, propylphenyl, butylphenyl, dibutylphenyl, pentylphenyl, hexylphenyl, heptylphenyl and octylphenyl.

Phenylalkyl is phenyl-substituted alkyl; $C_7$–$C_{11}$phenylalkyl embraces examples such as benzyl, α-methylbenzyl, α-ethylbenzyl, α,α-dimethylbenzyl, phenylethyl, phenylpropyl, phenylbutyl and phenylpentyl.

Glycidyl is 2,3-epoxypropyl. n-alkyl or alkyl-n is an unbranched alkyl radical.

Alkyl interrupted by O, NH, $NR_{13}$, etc., can generally comprise one or more nonadjacent heteroatoms. Preferably, a carbon atom of the alkyl chain bonds to not more than 1 heteroatom.

Within the scope of the stated definitions, the radicals $R_4$, $R_5$, $R_6$, $R_8$, $R_9$, $R_{11}$, $R_{12}$, $R_{13}$, $R_{14}$, $R_{15}$ and $R_{16}$ as alkyl branched or unbranched alkyl such as methyl, ethyl, propyl, isopropyl, n-butyl, sec-butyl, isobutyl, t-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl and octadecyl.

$C_1$–$C_4$alkyl is especially methyl, ethyl, isopropyl, n-butyl, 2-butyl, 2-methylpropyl or tert-butyl.

Within the scope of the stated definitions, $R_4$, $R_5$, $R_6$, $R_8$, $R_9$, $R_{11}$, $R_{12}$, $R_{13}$, $R_{14}$, $R_{15}$ and $R_{16}$ as alkenyl include allyl, isopropenyl, 2-butenyl, 3-butenyl, isobutenyl, n-penta-2,4-dienyl, 3-methyl-but-2-enyl; $R_8$ further includes n-oct-2-enyl, n-dodec-2-enyl, isododecenyl, n-octadec-2-enyl and n-octadec-4-enyl. In the case of $R_{12}$ and $R_{15}$, for example, vinyl is another possible definition.

$R_4$, $R_5$ and $R_6$, independently, are preferably $C_1$–$C_{18}$alkyl; $C_5$–$C_{12}$cycloalkyl; $C_2$–$C_{18}$alkenyl; phenyl; $C_7$–$C_{11}$phenylalkyl; $C_7$–$C_{11}$alkylphenyl; $C_1$–$C_{18}$alkyl substituted by OH, $C_1$–$C_{18}$alkoxy, $C_5$–$C_{12}$cycloalkoxy, COOH, $COOR_{11}$, O—$COR_{12}$, $CONH_2$, $CONHR_{13}$, $CONR_{13}R_{14}$, CN; or $R_5$ $C_5$–$C_{12}$cycloalkoxy, COOH, $COOR_{11}$, O—$COR_{12}$, $CONH_2$, $CONHR_{13}$, $CONR_{13}R_{14}$, CN; or $R_5$ and $R_6$ together with the carbon atom, they are attached to, form a $C_4$–$C_8$cycloalkyl ring or by O, NH, $NR_{13}$, S interrupted and/or by $C_1$–$C_6$alkyl, OH, phenoxy or $C_7$–$C_{18}$alkylphenoxy substituted $C_4$–$C_8$cycloalkyl ring;

$R_4$, $R_5$ and $R_6$ are more preferably $C_1$–$C_8$alkyl; cyclohexyl; $C_2$–$C_3$alkenyl; phenyl; benzyl; $C_1$–$C_8$alkyl substituted by OH, $C_1$–$C_8$alkoxy, cyclohexyloxy, COOH, $COOR_{11}$ or O—$COR_{12}$; or $R_5$ and $R_6$ together with the carbon atom, they are attached to, are $C_4$–$C_8$cycloalkyl or $C_4$–$C_8$cycloalkyl interrupted by O and/or substituted by $C_1$–$C_6$alkyl; $R_4$, $R_5$ and $R_6$ are especially methyl.

$R_8$ and $R_{11}$ preferably are $C_1$–$C_{18}$alkyl; $C_2$–$C_{16}$alkenyl; $C_5$–$C_{12}$Cycloalkyl; $C_6$–$C_{14}$alkylcyclohexyl; $C_6$–$C_{14}$aryl; $C_7$–$C_{11}$phenylalkyl; $C_7$–$C_{14}$alkylphenyl; or is $C_3$–$C_{30}$alkyl interrupted by O, NH, $NR_{13}$ or S and/or substituted by OH, phenoxy, $C_3$–$C_{18}$alkenoxy, $C_7$–$C_{18}$alkylphenoxy, O—$COR_{12}$, O—P(=O)$(OR_{12})_2$, O—P(=O)$(R_{12})_2$, or O—Si$(OR_{12})_3$; or is $CH_2$—CH(OH)—$R_{17}$, furfuryl or tetrahydrofurfuryl; more preferred are long-chain radicals, examples being those containing 5 to 50 carbon atoms, especially if $R_4$, $R_5$ and $R_6$ are short-chain radicals such as methyl; particular interest attaches to $C_5$–$C_{18}$alkyl; $C_7$–$C_{11}$phenylalkyl; $C_7$–$C_{14}$alkylphenyl; or $C_5$–$C_{30}$alkyl interrupted by O, NH, $NR_{13}$ or S and/or substituted by OH, phenoxy, $C_3$–$C_{18}$alkenoxy, $C_7$–$C_{18}$alkylphenoxy, O—$COR_{12}$, O—P(=O)$(OR_{12})_2$, O—P(=O)$(R_{12})_2$ or O—Si$(OR_{12})_3$; or $CH_2$—CH(OH)—$CH_2$—O—$R_{15}$, where $R_{15}$ is $C_3$–$C_{18}$alkyl or $C_5$–$C_{12}$cycloalkyl; $C_7$–$C_{11}$phenylalkyl; $C_7$–$C_{14}$alkylphenyl; particular preference as $R_8$ and $R_{11}$ attaches to $C_6$–$C_{18}$alkyl, $C_7$–$C_{14}$phenylalkyl; or $CH_2$–CH(OH)—$CH_2$—O—$R_{15}$, where $R_{15}$ is $C_3$–$C_{18}$alkyl.

Within certain compositions defined below, $R_9$ also may be methyl or ethyl. $R_9$ is preferably $C_3$–$C_{18}$alkyl; $C_3$–$C_{18}$alkenyl; $C_5$–$C_{12}$cycloalkyl; $C_1$–$C_4$alkyl-cyclohexyl; $C_6$–$C_{14}$aryl; $C_7$–$C_{11}$phenylalkyl; $C_7$–$C_{14}$alkylphenyl; more preferably $C_4$–$C_{18}$alkyl, $C_5$–$C_{12}$cycloalkyl or benzyl; especially $C_6$–$C_{12}$alkyl. $R_9$ is preferably a relatively long-chain radical containing, for example, 4–18, especially 5–18 and, in particular, 6–12 carbon atoms.

X and Y independently of one another are preferably O, NH or $NR_{13}$; with particular preference, X is O, NH or $NR_{13}$ and Y is oxygen; with especial preference, X and Y are O.

With particular preference $R_{13}$ is $C_3$–$C_8$alkyl, $C_5$–$C_{12}$cycloalkyl or benzyl, especially butyl or cyclohexyl.

$R_7$ as a radical of the formula III is with particular preference of the formula:

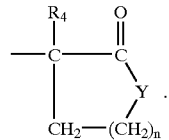

Special interest attaches to those compounds of the formula I in which $R_7$ is a radical of the formula III or IV, with the exception of the compound 2,4,6-tris(2-hydroxy-4-[1- ethyloxycarbonyl-1-methylethoxy]phenyl)-1,3,5-triazine. In the position α in respect to the $R_7$-substituted-oxygen-atom-in formula II and to the carbonyl group in formula III or IV these preferred compounds contain a quaternary carbon atom which does not bond to hydrogen.

Particularly preferred forms of this embodiment are analogous to those set out later on below.

The compounds of the formula I can be prepared in analogy to one of the methods indicated in EP-A-434608, one of the publications specified at the outset, or in the publication by H. Brunetti and C. E. Lüthi, Helv. Chim. Acta 55, 1566 (1972), by Friedel-Crafts addition of halotriazines with corresponding phenols; see also U.S. Pat. No. 3,118,887 and EP-A-165608. This can be followed by a further, conventional reaction to give compounds of the formula I in which $R_7$ is other than hydrogen; such reactions and methods are described, for example, in EP-A-434608, page 15, line 11, to page 1.7, line 1.

To prepare compounds of the formula I it is judicious to start from one equivalent of cyanuric chloride and to react it with three equivalents of resorcinol.

The reaction takes place in a conventional manner by reacting the starting materials in an inert solvent in the presence of anhydrous $AlCl_3$. In this reaction, aluminium trichloride and resorcinol are judiciously employed in excess; for example, aluminium trichloride.can be used in 5–15% molar excess and the phenol in a molar excess of 1–30%, especially in 5–20%.

Examples of suitable solvents are simple hydrocarbons, chlorinated hydrocarbons, hydrocarbons containing SO— or $SO_2$ groups, or nitrogenated aromatic hydrocarbons; preference is given to high-boiling hydrocarbons such as ligroin, petroleum ether, toluene or xylene, or sulfolane.

The temperature is generally not critical; usually, reaction takes place at temperatures between 20° C. and the boiling point of the solvent, for example between 50° C. and 150° C. The product can be worked up by conventional methods, such as by extraction and separation steps, filtration and drying; if required, further purifying steps can be performed, such as recrystallization.

Free phenolic hydroxyl groups in the reaction product that are positioned para to the triazine ring can be subjected subsequently to conventional etherification.

For instance, compounds of the formula I in which $R_7$ is a radical of the formula III or IV or V can be prepared advantageously by reacting the said phenolic intermediate with an α-halogenated lactone or ester of the formula III-Hal or IV-Hal or V-Hal

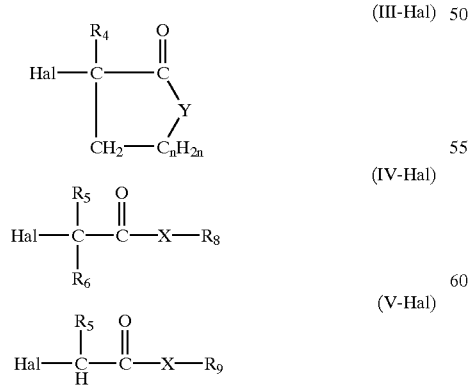

where Hal is a halogen atom, for example Cl or Br, preferably Br; the other symbols are as defined above. The reaction is judiciously conducted in the presence of an acid-binding agent and an appropriate solvent. The use of aprotic solvent such as diglyme, for example, is advantageous. The solvents are preferably dimethylsulfoxide, dimethylformamide, dimethylacetamide, acetone, ethyl methyl ketone, ethanol, methanol, isopropanol, diglyme, toluene, xylene, or mixtures thereof. Acid-binding agents which have proved suitable include bases such as carbonates and bicarbonates or alcoholates such as $Na_2CO_3$, $K_2CO_3$, sodium ethoxide, sodium methoxide or potassium tert-butoxide.

In the stated reactions, heating frequently takes place to a temperature range of 80–200° C., judiciously in the presence of an appropriate solvent, such as an aprotic solvent. For example, reaction ii) can be conducted with triphenylethylphosphonium bromide at 150° C. in mesitylene.

Preparation of compounds of the formula I may first lead to mixtures, which may directly be used as stabilisers without purification of the compound of formula I. These with advantage usable mixtures are obtained by reacting 1 mol of the starting phenol 2,4,6-tris(2,4-dihydroxyphenyl)-1,3,5-triazine with excess of halogenated educt of formula III-Hal, IV-Hal or IV-Hal, e.g. by starting from 1 mol of the starting phenol and 3–4 moles of the halogenated educt. Examples are product mixtures containing, besides the compound of formula I of the invention (obtained by reaction of the starting phenol 2,4,6-tris(2,4-dihydroxyphenyl)-1,3,5-triazine with 3 equivalents halogenated educt of formula III-Hal, IV-Hal or IV-Hal), a 4- or 5-fold reacted product. A 4-fold reacted product within this mixture is, for example, the compound obtained from conversion of 1 mol of the starting phenol and 4 moles of the halogenated educt, which corresponds to the compounds of GB-A-2319523, formula I, pages 1–3.

These mixtures are advantageously employed as UV absorbers in wood coatings, stains or impregnations on wood, or in automotive coatings, especially in the base coat.

Preference is given to novel compounds of the formula I in which $R_7$ is a radical of the formula II, IV or V and $R_4$, $R_5$ and $R_6$, independently of one another are $C_1$–$C_{18}$alkyl; $C_5$–$C_{12}$cycloalkyl; $C_2$–$C_{16}$alkenyl; phenyl; $C_7$–$C_{11}$phenylalkyl; $C_7$–$C_{11}$alkylphenyl; $C_1$–$C_{18}$alkyl substituted by phenyl, $C_1$–$C_{18}$alkoxy, $C_5$–$C_{12}$cycloalkoxy, $C_3$–$C_{18}$alkenyloxy or $C_6$–$C_{15}$bicycloalkyl; or $COR_{15}$; CO—X—$R_{11}$; or $SO_2$—$R_{16}$; or are $C_3$–$C_{50}$alkyl interrupted by O and/or substituted by OH, phenoxy, or $C_7$–$C_{18}$alkylphenoxy;

or $R_5$ and $R_6$, together with the carbon atom to which they are attached, form a $C_5$–$C_6$cycloalkyl ring which is uninterrupted or interrupted by O, NH, $NR_{13}$ and/or unsubstituted or substituted by $C_1$–$C_6$alkyl, OH, phenoxy or $C_7$–$C_{18}$alkylphenoxy;

$R_8$ is as defined for $R_{11}$; $R_9$ is $C_6$–$C_{12}$alkyl, $C_6$–$C_{12}$cycloalkyl or $C_7$–$C_{12}$phenylalkyl;

$R_{11}$ is $C_1$–$C_{18}$alkyl; $C_2$–$C_{18}$alkenyl; $C_{5-C12}$cycloalkyl; phenyl; $C_7$–$C_{11}$phenylalkyl; $C_7$–$C_{14}$alkylphenyl; or $C_3$–$C_{30}$alkyl interrupted by O and/or substituted by OH, phenoxy, O—$COR_{12}$, O—$P(=O)(OR_{12})_2$, O—P$(=O)(R_{12})_2$, O—$Si(OR_{12})_3$; or is $CH_2$—CH(OH)—$R_{17}$, futuryl or tetrahydrofurfuryl;

$R_{12}$ is $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; $C_6$–$C_{15}$bicycloalkyl; $C_6$–$C_{15}$bicycloalkenyl or $C_6$–$C_{15}$tricycloalkyl;

$R_{13}$ and $R_{14}$ independently of one another are $C_1$–$C_{18}$alkyl; allyl; $C_5$–$C_{12}$cycloalkyl; phenyl;

$C_7$–$C_{11}$phenylalkyl; $C_7$–$C_{14}$alkylphenyl; or $C_3$–$C_{30}$alkyl interrupted by O and/or substituted by OH; or are $C_6$–$C_{15}$bicycloalkyl; $C_6$–$C_{15}$bicycloalkenyl; or $C_6$–$C_{15}$tricycloalkyl;

$R_{15}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{16}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{17}$ is $CH_2$—O—$R_{15}$, furfuryl or tetrahydrofurfuryl or is $C_3$–$C_{30}$alkyl interrupted by O and/or substituted by OH; and X and Y independently of one another are O, NH or $NR_{13}$.

Particular preference is given to novel compounds of the formula I in which $R_7$ is a radical of the formula IV or V and $R_5$ is $C_1$–$C_{18}$alkyl; phenyl; or $C_7$–$C_{11}$henylalkyl; $R_6$ is $C_1$–$C_{18}$alkyl; phenyl; $C_7$–$C_{11}$phenylalkyl; $COR_{15}$ or CO—X—$R_{11}$; or $R_5$ and $R_6$, together with the carbon atom to which they are attached, form a $C_5$–$C_6$cycloalkyl ring which is uninterrupted or interrupted by O and/or unsubstituted or substituted by $C_1$–$C_6$alkyl; $R_8$ is as defined for $R_{11}$; $R_9$ is $C_6$–$C_{12}$alkyl, $C_6$–$C_{12}$cycloalkyl or $C_7$–$C_{12}$phenylalkyl; $R_{11}$ is $C_1$–$C_{18}$alkyl; allyl; $C_5$–$C_{12}$cycloalkyl; phenyl; $C_7$–$C_{11}$phenylalkyl; $C_7$–$C_{14}$alkylphenyl; or is $C_3$–$C_{30}$alkyl interrupted by O, NH or $NR_{13}$ and/or substituted by OH, phenoxy, O—$COR_{12}$, O—P(=O)$(OR_{12})_2$, O—P(=O)$(R_{12})_2$ or O—Si$(OR_{12})_3$; $R_{12}$ is $C_1$–$C_{18}$alkyl; $C_2$–$C_{18}$alkenyl; cyclohexyl; phenyl; or $C_7$–$C_{11}$phenylalkyl; $R_{13}$ and $R_{14}$ independently of one another are $C_1$–$C_{18}$alkyl; allyl; $C_5$–$C_{12}$cycloalkyl; phenyl; or $C_7$–$C_{11}$phenylalkyl; and $R_{15}$ is $C_1$–$C_{18}$alkyl; $C_2$–$C_3$alkenyl; cyclohexyl; phenyl; $C_7$–$C_{11}$phenylalkyl; or $C_7$–$C_{14}$alkylphenyl.

Of particular importance are compounds of the formula I in which $R_7$ is a radical of the formula IV or V and $R_5$ is $C_1$–$C_{18}$alkyl; phenyl; or $C_7$–$C_{11}$phenylalkyl; $R_6$ is $C_1$–$C_{18}$alkyl; phenyl; $C_7$–$C_{11}$phenylalkyl; $COR_{16}$ or CO—X—$R_{11}$; or $R_5$ and $R_6$, together with the carbon atom to which they are attached, form a $C_5$–$C_6$cycloalkyl ring; $R_8$ is as defined for $R_{11}$; $R_9$ is $C_5$–$C_{12}$alkyl, cyclohexyl or cyclododecyl; $R_{11}$ is $C_1$–$C_{18}$alkyl; allyl; $C_5$–$C_{12}$cycloalkyl; phenyl; $C_7$–$C_{11}$phenylalkyl; $C_7$–$C_{14}$alkylphenyl; or is $C_3$–$C_{30}$alkyl interrupted by O and/or substituted by OH, phenoxy, O—$COR_{12}$, O—P(=O)$(OR_{12})_2$, O—P(=O)$(R_{12})_2$ or O—Si$(OR_{12})_3$; $R_{12}$ is $C_1$–$C_8$alkyl; $C_2$–$C_3$alkenyl; phenyl; or benzyl; and $R_{15}$ is $C_1$–$C_{18}$alkyl; $C_2$–$C_3$alkenyl; cyclohexyl; phenyl; or benzyl and X is O or $NR_{13}$ or NH;

especially those in which $R_7$ is a radical of the formula IV or V and $R_5$ is $C_1$–$C_4$alkyl; $R_6$ is $C_1$–$C_4$alkyl; $R_8$ is as defined for $R_{11}$; $R_9$ is $C_6$–$C_{12}$alkyl; $R_{11}$ is $C_1$–$C_{18}$alkyl; benzyl; or is $C_3$–$C_{30}$alkyl interrupted by O and/or substituted by OH, O—$COR_{12}$, or O—Si$(OR_{12})_3$; $R_{12}$ is $C_1$–$C_8$alkyl; and $R_{13}$ is $C_1$–$C_{12}$alkyl or cyclohexyl.

Particularly preferred compounds are those in which X is oxygen.

The invention additionally provides compositions comprising

A) an organic material sensitive to exposure to light, oxygen and/or heat, and

B) as stabilizer, a compound of the formula I, and provides a method of stabilizing organic material against exposure to light, oxygen and/or heat, which comprises admixing or applying to said material as stabilizer a compound of the formula I, and provides for the use of a compoud of the formula I as a stabilizer against exposure to light, oxygen and/or heat.

Such materials to be stabilized in accordance with the invention by adding a compound of the formula I can, for example, be oils, fats, waxes, photographic material, cosmetics or biocides. Particular interest attaches to use in polymeric materials, as present in plastics, rubbers, coating materials and adhesives. Where the material to be stabilized is photographic material its structure is preferably as described in the U.S. Pat. No. 5,538,840 from column 25 line 60 to column 106 line 35 and the novel compound of the formula I is used in analogy to the compound of the formula (I) described in U.S. Pat. No. 5,538,840 or polymers prepared from it; the cited sections of U.S. Pat. No. 5,538,840 are considered incorporated into the present description.

Preferred materials which can be stabilized in accordance with the invention are synthetic organic polymers, prepolymers, and photographic material. By the said prepolymers are meant those monomeric or oligomeric compounds which can be converted into the high molecular mass form (polymer) under the influence of heat or radiation, such as UV radiation, electron beams or X-rays, and/or under the influence of chemical components such as crosslinkers, couplers or catalysts.

The invention additionally provides the use of compounds of the formula I as stabilizers for synthetic organic polymers or prepolymers or photographic material against their damage by light, oxygen or heat. The compounds of the formula I are especially suitable as light stabilizers (UV absorbers). Particular interest attaches to their use in synthetic organic polymers or prepolymers as present in plastics, rubbers and adhesives and, in particular, in coating materials. Examples of polymers which can be stabilized in this way are as follows:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and a elevate temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either λ- or σ coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylenetvinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly($\alpha$-methylstyrene).

6. Copolymers of styrene or $\alpha$-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures. of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamins, on-the-other-hand,such-as-phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.

28. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.

The amount of stabilizer to be used depends on the organic material to be stabilized and on the intended use of the stabilized material. In general the composition of the invention contains from 0.01 to 15, in particular from 0.05 to 10 and, especially, from 0.1 to 5 parts by weight of the stabilizer (component B) per 100 parts by weight of component A.

Alongside the stabilizer of the formula I the compositions of the invention may also include other stabilizers or other additives, such as antioxidants, further light stabilizers, metal deactivators, phosphites and phosphonites. Examples of these are the following stabilizers:

1. Antioxidants 1.1. Alkylated monophenols, for example 2,6-di-tert-butyl4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol,2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl)adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2°-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-teirt-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbarnate.

1.13. Esters of β-(3.5-di-tert-butyl-4-hydroxyohenyl) propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or poly-hydric alcohols, e.g. with methanol, ethanol, notanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15. Esters of β-(3.5-dicyclohexyl-4-hydroxyphenyl) propionic acid with mono- or poly-hydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3.5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxphenyl]propionyloxy)ethyl]oxamide (Naugard®XL-1 supplied by Uniroyal).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1',3'-dimethylbutyl) phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butytdiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl) sebacate, 2,2,6,6-tetramethylpiperidin-4-one, 2,2,6,6-tetramethylpiperin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotdazole, 2-(5'-tertbutyl-2'-hydroxyphenyl)benzotrazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl) benzotriazole, 2-(2'-hydroxy-4'-octyloxyphenyl) benzotriazole, 2-(3',5'-di-tert-amyl-2'-hydroxyphenyl) benzotriazole, 2-(3',5'-bis-(α,α-dimethylbenzyl)-2'-hydroxyphenyl)benzotriazole, 2-(3'-tert-butyl-2'-hydroxy-5'-(2octyloxycarbonylethyl)phenyl)-5-chloro-benzotriazole, 2-(3'-tert-butyl-5'-[2-(2-ethylhexloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)

benzotriazole, 2-(3'-tert-butyl-5'-[2-(2-ethylhexyloxy) carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO—CH$_2$CH$_2$—] where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-tmhydroxy and 2'-hydroxy-4,4'-dimethoxy derivatives.

2.3. Esters of substituted and unsubstituted benzoic acids, as for example 4tertbutyl-phenyl salicylate, phenyl salicylate, octyiphenyl salicylate, dibenzoyl resorcinol, bis(4-tert-butylbenzoyl)resorcinol, benzoyl resorcinol, 2,4di-tert-butylphenyl 3,5-di-tert-butyl4-hydroxybenzoate, hexadecyl 3,5-di-tert-butyl4-hydroxybenzoate, octadecyl 3,5-di-tert-butyl-4-hydroxybenzoate, 2-methyl-4,6-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbarnate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl)n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperdyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl) sebacate, bis(1-octyloxy-2,2,6,6-tetramethylpiperidyl) succinate, linear or cyclic condensates of N,N'-bis-(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino1,2,2,6,6pentamethylpiperdyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6.6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimid, N-(1,2,2,6,6-pentamethyl-4-piperidyl)-n-dodecylsuccnimid, 2-undecyl7,7,9,9-tetramethyl-1-oxa-3,8-diaza-4-oxo-spiro [4,5]decane, a reaction product of 7,7,9,9-tetramethyl-2-cyclounde-cyl-1-oxa-3,8-diaza-4-oxospiro [4,5]decane und epichlorohydrin, 1,1-bis(1,2,2,6,6-pentamethyl-4-piperidyloxycarbonyl)-2-(4-methoxyphenyl)ethene, N,N'-bis-formyl-N,N'-bis(2,2,6,6-tetramethyl-4-piperidyl) hexamethylenediamine, diester of 4-methoxy-methylene-malonic acid with 1,2,2,6,6-pentamethyl-4-hydroxypiperidine, poly[methylpropyl-3-oxy4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy) phenyl]-4,6-bis(2,4-dimethyl)-1,3,5-trazine, 2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy) phenyl4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N-N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl)4,4'-biphenylene diphosphonite, 6-isooctyloxy-2,4,8,10-tetra-tert-butyl-12H-dibenz-[d,g]-1,3,2-dioxaphosphocin, bis(2,4-di-tert-butyl-6-methylphenyl)methyl phosphite, bis(2,4-di-tert-butyl-6-methylphenyl)ethyl phosphite, 6-fluoro-2,4,8,10-tetra-tert-butyl-12-methyl-di-benz[d,g]-1,3,2-dioxaphosphocin, 2,2',2"-nitrilo[triethyltris(3,3',5,5'-tetra-tert-butyl-1,1'-biphenyl-2,2'-diyl)phosphite], 2-ethylhexyl (3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

Especially preferred are the following phosphites:

Tris(2,4-di-tert-butylphenyl)phosphite (Irgafos®168, Ciba-Geigy), tris(nonylphenyl)phosphite,

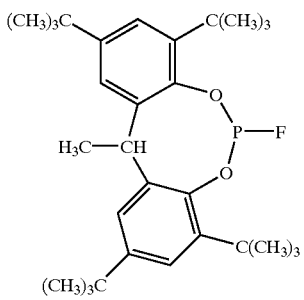

(A)

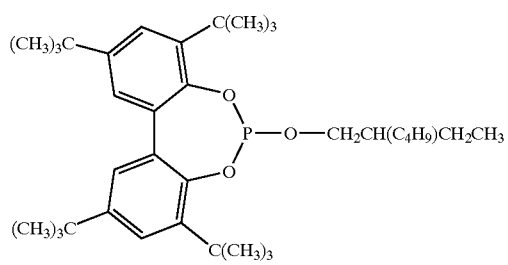

(C)

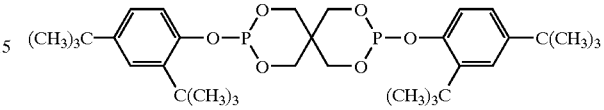

(D)

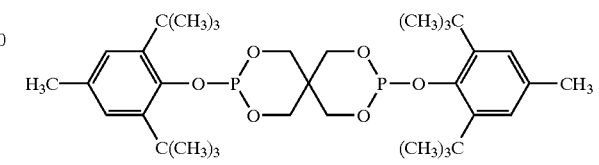

(E)

(F)

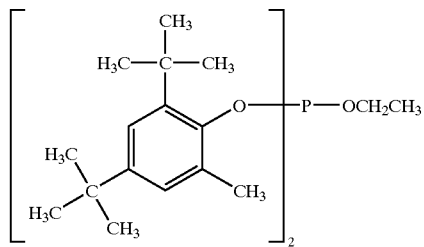

(B)

(G)

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxyldiine, N-hexadecyl-N-octadecylhydroxylamine, N-heptadecyl-N-octadecylhydroxylamine, N,N-dialkylhydroxylamine derived from hydrogenated tallow amine.

6. Nitrones for example, N-benzyl-alpha-phenyl-nitone, N-ethyl-alpha-methyl-nitrone, N-octyl-alpha-heptyl-nitrone, N-lauryl-alpha-undecyl-nitrone, N-tetradecyl-alpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived frofm N,N-dialkylhydroxylamine derived from hydrogenated tallow amine.

7. Thiosyneraists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbarnate, dioctadecyl disulfide, pentaerythritol tetrakis(β-dodecylmercapto)propionate.

9. Polvamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers). Especially preferred are 1,3:2,4-bis(3',4'-dimethylbenzylidene)sorbitol, 1,3:2,4-di(paramethyldibenzylidene)sorbitol, und 1,3:2,4-di(benzylidene)sorbitol.

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinonds, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-di-methylphenyl)-5,7-di-tert-butyl-benzofuran-2-one.

The nature and amount of the further stabilizers added are determined by the nature of the substrate to be stabilized and its intended use; in many cases from 0.1 to 5% by weight is used, based on the polymer to be stabilized.

With particular advantage the compounds of the formula I can be employed in compositions which comprise as component A a synthetic organic polymer, in particular a thermoplastic polymer, a binder for coatings such as paints, for example, or a reprographic material, especially a photographic material.

In cases where the substrate to be stabilized is a synthetic organic polymer or prepolymer, especially as indicated above, the composition of the invention may also include the compound which was the subject of the earlier exception (2,4,6-tris(2-hydroxy-4-[1-ethyloxycarbonyl-1-methylethoxy]phenyl)-1,3,5-triazine) or short chain $R_9$ (methyl or ethyl).

In cases where the substrate to be stabilized is a photographic material or a component thereof, such as a colour coupler, and does not contain a compound of the formula XV

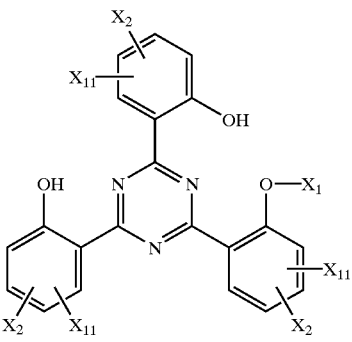

(XV)

in which XI is a hydrocarbon radical with or without heteroatoms and $X_2$ and $X_{11}$ independently of one another are hydrogen or are likewise hydrocarbon radicals with or without heteroatoms, the composition of the invention can also include the compound which was the subject of the earlier exception (2,4,6-tris(2-hydroxy4-[1-ethyloxycarbonyl-1-methylethoxy]phenyl)-1,3,5-triazine) or short chain $R_9$ (methyl or ethyl).

Preferred compounds within these compositions are as described above.

The reprographic material to be stabilized with advantage in accordance with the present invention, especially colour photographic material, is, for example, that described in Research Disclosure 1990, 31429 (pages 474–480), in U.S. Pat. No. 5,538,840 columns 26 to 106, in GB-A-2319523 or DE-A-19750906, page 22, line 15 to page 105, line 32. Preference is given to use in a layer containing silver halide or in the protective layer of a colour photographic material, especially a colour film or colour photographic paper.

Examples of suitable thermoplastic polymers are polyolefins (e.g. in accordance with items 1.–3. in the above list) and polymers containing heteroatoms in the main chain, such as thermoplastic polymers containing nitrogen, oxygen and/or sulfur, especially nitrogen or oxygen, in the main chain; examples of such polymers are given in the above list, inter alia, under items 13.–20. and among these particular importance attaches to polyamides, polyesters and polycarbonate (17.–19.).

Incorporation into the synthetic organic polymers or prepolymers can take place by adding the compounds of the invention, with or without any further additives, by the methods customary in the art. Incorporation can take place judiciously prior to or during the shaping operation, for example by mixing the pulverulent components or by adding the stabilizer to the melt or solution of the polymer, or by applying the dissolved or dispersed compounds to the polymer, with or without subsequent evaporation of the solvent. In the case of elastomers, these can also be stabilized as latices. Another possibility for incorporating the compounds of the invention into polymers is to add them prior to or during the polymerization of the corresponding monomers and/or prior to crosslinking.

The compounds of the invention or mixtures thereof can also be added in the form of a masterbatch which contains these compounds in a concentration, for example, of from 2.5 to 25% by weight to the plastics that are to be stabilized.

The compounds of the invention can judiciously be incorporated by the following methods:

as an emulsion or dispersion (e.g. to latices or emulsion polymers)

as a dry mixture during the mixing of additional components or polymer mixtures bydirect addition to the processing apparatus (e.g. extruders, internal mixers, etc.) as a solution or melt.

The stabilized polymer compositions obtained in this way can be converted by the customary methods, such as by hot pressng, spinning, extrusion or injection moulding, into shaped articles, for example fibres, films, strips, sheets, sandwich boards, vessels, pipes and other profiles.

The invention therefore additionally provides for the use of the polymer composition of the invention for producing a shaped article.

Also of interest is the use in multilayer systems. In this case a polymer composition of the invention containing a relatively large amount of stabilizer of the formula 1, for example 1–15% by weight, is applied in a thin layer (10–100 μm) to a shaped article made from a polymer containing little or no stabilizer of the formula 1. Application can be made at the same time as the shaping of the base article, for example by coextrusion. Alternatively, application can be made to the base article after it has been shaped, for example by lamination with a film or by coating with a solution. The external layer or layers of the finished article has or have the function of a UV filter which protects the interior of the article against UV light. The external layer contains preferably 1–15% by weight, especially 5–10% by weight, of at least one stabilizer of-the formula I.

The use-of the polymer compositionof the invention to produce multilayer systems in which the outer layer(s) in a thickness of 10–100 μm consist(s) of a polymer composition of the invention while the inner layer contains little or no stabilizer of the formula I is therefore also provided by the invention.

The polymers stabilized in this way feature high weathering stability and, in particular, high stability to UV light. As a result, even during long-term outdoor service, they retain their mechanical properties and also their colour and lustre.

Of particular interest is the use of the novel compounds of the formula I as stabilizers for .coatings, for example paints.- The invention therefore also provides those compositions whose component A is a film-forming binder or impregnation for coatings.

The-novel-coating compositionpreferably comprises 0.01–10 parts by weight of (B), in particular 0.05–10 parts by weight of (B), especially 0.1–5 parts by weight of (B), per 100 parts by weight of solid binder (A).

Multilayer systems are possible here as well, where the concentration of the novel stabilizer (component (B)) in the outer layer can be relatively high, for example from 1 to 15 parts by weight of (B), in particular 3–10 parts by weight of (B), per 100 parts by weight of solid binder (A).

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates.

The binder (component (A)) can in principle be any binder which is customary in industry, for example those described in Ullmann's Encyclopedia of Industrial Chemistry, 5th Edition, Vol. A18, pp. 368–426, VCH, Weinheim 1991. In general, it is a film-forming binder based on a thermoplastic or thermosetting resin, predominantly on a thermosetting resin. Examples thereof are alkyd, acrylic, polyester, phenolic, melamine, epoxy and polyurethane resins and mixtures thereof.

Component (A) can be a cold-curable or hot-curable binder; the addition of a curing catalyst may be advantageous. Suitable catalysts which accelerate curing of the binder are described, for example, in Ullmann's Encyclopedia of Industrial Chemistry, Vol. A18, p.469, VCH Verlagsgesellschaft, Weinheim 1991.

Preference is given to coating compositions in which component (A) is a binder comprising a functional acrylate resin and a crosslinking agent.

Examples of coating compositions containing specific binders are:

1. paints based on cold- or hot-crosslinkable alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking, if desired with addition of a melamine resin;
4. one-component polyurethane paints based on a Tris-alkoxycarbonyltriazine crosslinker and a hydroxyl group containing resin such as acrylate, polyester or polyether resins;
5. one-component polyurethane paints based on aliphatic or aromatic urethaneacrylates or polyurethaneacrylates having free amino groups within the urethane strukture and melamine resins or polyether resins, if necessary with curing catalyst;
6. two-component paints based on (poly)ketimines and aliphatic or aromatic isocyanates, isocyanurates or polyisocyanates;
7. two-component paints based on (poly)ketimines and an unsaturated acrylate resin or a polyacetoacetate resin or a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and acrylate resins containing anhydride groups, or unsaturated acrylate resins, or aliphatic or aromatic isocyanates, isocyanurates or polyisocyanates;
12. two-component paints- based-on unsaturated polyacrylates and polymalonates;
13. thermoplastic polyacrylate paints based on thermoplastic acrylate resins or externally crosslinking acrylate resins in combination with etherified melamine resins;
14. paint systems based on siloxane-modified or fluorine-modified acrylate resins.

In addition to components (A) and (B), the coating composition according to the invention preferably comprises as component (C) a light stabilizer of the sterically hindered amine type, the 2-(2-hydroxyphenyl)-1,3,5-triazine and/or 2-hydroxyphenyl-2H-benzotriazole type, for example as mentioned in the above list in sections 2.1, 2.6 and 2.8. Further examples for light stabilizers of the 2-(2-hydroxyphenyl)-1,3,5-triazine type advantageously to be added can be found e.g. in the publications U.S. Pat. No. 4,619,956, EP-A34608, U.S. Pat. No. 5,198,498, U.S. Pat.

No. 5,322,868, U.S. Pat. No. 5,369,140, U.S. Pat. No. 5,298,067, WO-94/18278, EP-A-704437, GB-A-2297091, WO-96/28431. Of special technical interest is the addition of the 2-(2-hydroxyphenyl)-1,3,5-triazines and/or 2-hydroxyphenyl-2H-benzotriazoles, especially the 2-(2-hydroxyphenyl)-1,3,5-triazines.

To achieve maximum light stability, it is of particular interest to add sterically hindered amines as set out in the abovementioned list under 2.6. The invention therefore also relates to a coating composition which in addition to components (A) and (B) comprises as component (C) a light stabilizer of the sterically hindered amine type.

This stabilizer is preferably a 2,2,6,6-tetraalkylpiperidine derivative containing at least one group of the formula

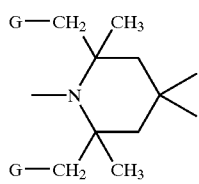

in which G is hydrogen or methyl, especially hydrogen.

Component (C) is preferably used in an amount of 0.05–5 parts by weight per 100 parts by weight of the solid binder.

Examples of tetraalkylpiperidine derivatives which can be used as component (C) are given in EP-A-356 677, pages 3–17, sections a) to f). These sections of this EP-A are regarded as part of the present description. It is particular expedient to employ the following tetraalkylpiperidine derivatives:

bis(2,2,6,6-tetramethylpiperid-4-yl)succinate, bis(2,2,6,6-tetramethylpiperid-4-yl)sebacate, bis(1,2,2,6,6-pentamethylpiperid-4-yl)sebacate, di(1,2,2,6,6-pentamethylpiperid-4-yl)butyl-(3,5-di-tert-butyl-4-hydroxybenzyl)malonate, bis(1-octyloxy-2,2,6,6-tetramethylpiperid-4-yl)sebacate, tetra(2,2,6,6-tetrarethylpiperd-4-yl)butane-1,2,3,4-tetracarboxylate, tetra(1,2,2,6,6-pentamethylpiperid-4-yl)butane-1,2,3,4-tetracarboxylate, 2,2,4,4-tetramethyl-7-oxa-3,20-diaza-21-oxo-dispiro [5.1.11.2]heneicosane, 8-acetyl-3-dodecyl-1,3,8-triaza-7,7,9,9-tetramethylspiro [4.5]decane-2,4-dione, 1,1-bis-(1,2,2,6,6-pentamethylpiperidine-4-yl-oxycarbonyl)-2-(4-methoxyphenyl)ethene, or a compound of the formulae

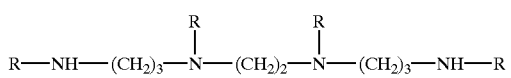

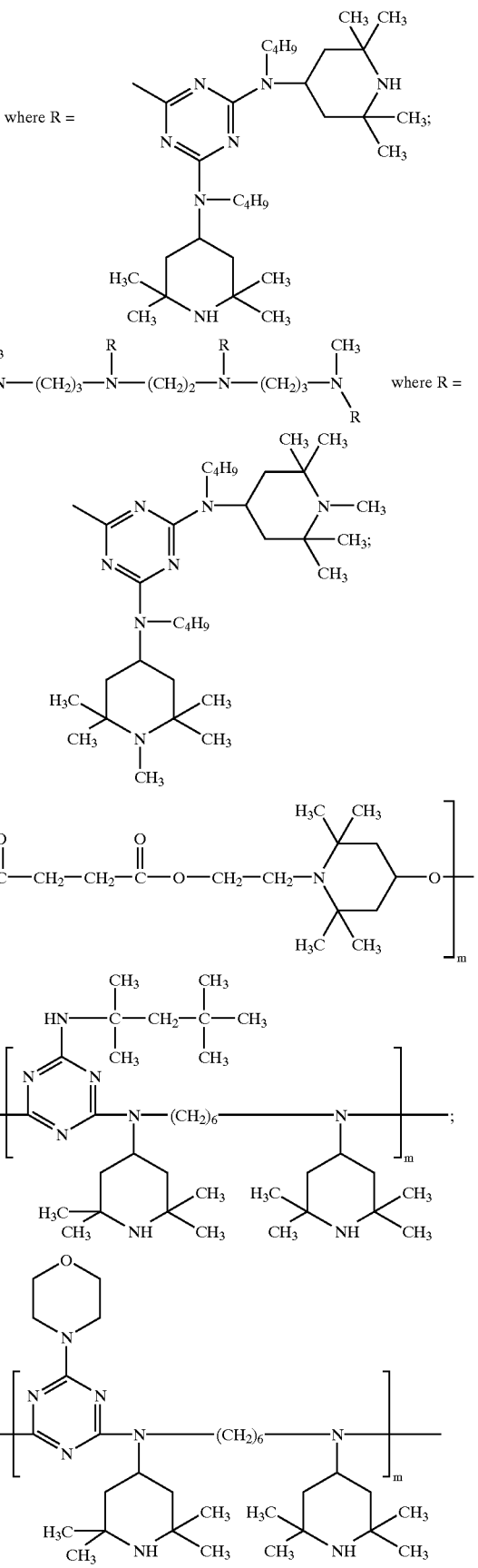

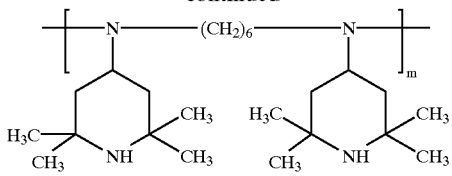

in which m is 5–50.

Apart from components (A), (B) and, if used, (C), the coating composition can also comprise further components, examples being solvents, pigments, dyes, plasticizers, stabilizers, thixotropic agents, drying catalysts and/or levelling agents. Examples of possible components are those described in Ullmann's Encyclopedia of Industrial Chemistry, 5th Edition, Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylates, especially those of the metals Pb, Mn, Co, Zn, Zr or Cu, or metal chelates, especially those of the metals Al, Ti or Zr, or organometallic compounds such as organotin compounds, for example.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoroacetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyst used can also be a phosphine, for example triphenylphosphine.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation curable coating compositions, the novel stabilizers can also be employed without the addition of sterically hindered amines.

The coating compositions according to the invention can be applied to any desired substrates, for example to metal, wood, plastic or ceramic materials. They are preferably used as base coat in the finishing of automobiles. If the topcoat comprises two layers, of which the lower layer is pigmented and the upper layer is not pigmented, the novel coating composition can be used for either the upper or the lower layer or for both layers, but preferably for the lower (pigmented) layer.

Also preferred is the use of present compounds for protecting a wood surface, e.g. by incorporation of a compound of the formula I into a varnish, paint, stain or impregnation on wood. Present invention therefore also pertains to a method for stabilizing a wood surface, e.g. a coating, especially a varnish, paint, stain or impregnation on wood, against harmful effects of light, oxygen and/or heat by incorporation or application of an effective stabilising amount of a compound of the formula I into or onto the wood. Compounds of present formula I effectively reduce the yellowing of the wood substrate. Compounds of the formula I may be applied as part of the stain or impregnation or as part of the top coat.

Applied on a wood substrate, it can be made use of a compound of the formula I wherein $R_9$ is as defined for $R_{11}$, e.g. compound 1 (2,4,6-tris(2-hydroxy-4-[1-ethyloxycarbonyl-1-methyl-ethoxy]-phenyl)-1,3,5-triazine). Preferred compounds are as defined above.

Often, a hindered amine compound is also present, preferably in an amount of 0.1–10%, more prefered 0.2–5% and most prefered 0.2–2% by weight based on the total weight of binder and solvent. Especially valuable in wood applications is a sterically hindered hydroxylamine, e.g. as described in EP-A-309401, or a corresponding N-oxide, as well as salts of these compounds.

In case that the wood coating is a stain or impregnation, preferably a solvent is used selected e.g. from the group consisting of aliphatic hydrocarbons, cycloaliphatic hydrocarbons, aromatic hydrocarbons, alcohols, ethers, esters, ketones, glycols, glycol ethers, glycol esters, polyglycols or mixtures thereof. Preferably in this case the binder is selected from the group consisting of alkyd resins, modified alkyd resins, autocrosslinking or non-autocrosslinking acrylic resins, polyester resins, drying oils, phenolic resins, nitrocellulose or mixtures thereof.

Usual additives like fungicides or insecticides are possible. Exemplary of useful fungicides are tributyltin oxide, phenylmercury salts, copper naphthenate, 1-chloronaphthalene or pentachlorophenol. Exemplary of useful insecticides are DDT, dieldrin, lindane, azaconazol, cypermethin, benzalkoniumhydrochloride, propiconazol or parathion.

Any coating composition suitable for coating wood may be used as additional top coat. It will normally contain a binder, dissolved or dispersed in an organic solvent or in water or a mixture of water and solvent. The binder may typically be a surface coating resin which dries in the air or hardens at room temperature. Exemplary of such binders are nitrocellulose, polyvinyl acetate, polyvinyl chloride, unsaturated polyester resins, polyacrylates, polyurethanes, epoxy resins, phenolic resins, and especially alkyd resins. The binder may also be a mixture of different surface coating resins. Provided the binders are curable binders, they are normally used together with the hardener and/or accelerator.

The top coat may also be a radiation-curable, solvent-free formulation of photopolymerisable compounds. Illustrative examples are mixtures of acrylates or methacrylates, unsaturated polyester/styrene mixtures or mixtures of other ethylenically unsaturated monomers or oligomers.

The top coat may contain a soluble dye and/or a pigment and/or a filler. The pigment may be an organic, inorganic or metallic pigment. The pigments may be opaque or transparent such as for example transparent iron oxides. The filler may be typically kaolin, calcium carbonate or aluminium silicate. Preferably the top coat is a clear varnish, i.e. it contains no undissolved components.

The present invention is particularly useful for the following applications: in house applications, such as furniture, parquet floors, chipards or timber work; outdoor applications such as fences, construction parts, wooden fronts, window frames and the like.

In cases where maximum stabilization is required a complete wood protection system may be applied. The wood protection system comprises an impregnation according to the present invention, optionally an intermediate layer and a final top coat, which may be stabilized as described before.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. The coatings are preferably cured at 50–150° C., and in the case of powder coatings or coil coatings even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula (I) according to the invention. The paint is preferably a base coat for automobiles or a wood coating. The invention furthermore relates to a process for stabilizing a coating based on organic polymers against damage by light, oxygen and/or heat, which comprises mixing with the coating composition a mixture comprising a compound of the formula (I), and to the use of mixtures comprising a compound of the formula (I) in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition may be a high-solids paint or can be solvent-free (e.g. a powder coating material). Powder coatings are, for example, those described in Ullmann's Encyclopedia of Industrial Chemistry, 5th Ed., A18, pages 438–444. The powder coating material may also have the form of a powder-slurry (dispersion of the powder preferably in water).

The pigments can be inorganic, organic or metallic pigments. The novel coating compositions preferably contain no pigments and are used as a clearcoat.

Likewise preferred is the use of the coating composition as a base coat for applications in the automobile industry, especially as a pigmented coat of the paint finish. Its use for topcoats, however, is also possible.

The stabilizer (component B) can also be a mixture of two or more compounds of the formula I.

The examples which follow describe the invention further without constituting any restriction. Parts and percentages therein are by weight; an example which mentions room temperature means thereby a temperature in the range 20–25° C. In the case of solvent mixtures such as those for chromatography the parts indicated are by volume. These definitions apply unless specified otherwise.

The following abbreviations are used:

| | |
|---|---|
| THF | tetrahydrofuran |
| abs. | anhydrous |
| m.p. | melting point or melting range |
| NMR | nuclear magnetic resonance |
| torr = | torricelli; mmHg (1 torr is about 133 Pa) |
| $T_g$ | glass transition temperature; h: hours. |

The following compounds are examples of compounds of the formula I; the suffix -n denotes in each case a straight-chain radical, the suffix -i a mixture of different isomeric radicals:

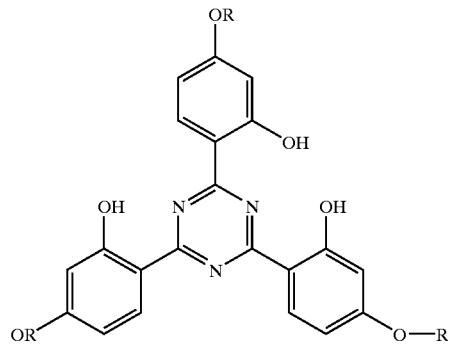

| No. | R = | m.p./° C. |
|---|---|---|
| (1) | $C(CH_3)_2$—CO—O—$C_2H_5$ | 150 |
| (2) | $C(CH_3)_2$—CO—O—$CH_3$ | 131 |
| (3) | $C(CH_3)_2$—CO—O—$(CH_2)_3$—$CH_3$ | 86–91 |
| (4) | $C(CH_3)_2$—CO—O—$(CH_2)_7$—$CH_3$ | 48–49 |
| (5) | $C(CH_3)_2$—CO—O—$(CH_2)_5$—$CH_3$ | 71–73 |
| (6) | $C(CH_3)_2$—CO—O—$(CH_2)_6$—$CH_3$ | 56–57 |
| (7) | $C(CH_3)_2$—CO—O—$(CH_2)_{11}$—$CH_3$ | 53–54 |
| (8) | $C(CH_3)_2$—CO—O—$CH_2$—$CH_2O$—$CH_3$ | 98–101 |
| (9) | $C(CH_3)_2$—CO—O—$(CH_2$—$CH_2O)_2$—$C_2H_5$ | 47–48 |
| (10) | $C(CH_3)_2$—CO—O—$(CH_2$—$CH_2O)_3$—$C_2H_5$ | 42–44 |
| (11) | $C(CH_3)_2$—CO—O—$C_8H_{17}$-i | 55–56 |
| (12) | $C(CH_3)_2$—CO—NH—$C_6H_{13}$-n | |
| (13), (14) | $C(CH_3)_2$—CO—NH—$C_6H_{13}$-n/$C(CH_3)_2$—CO—O—$C_2H_5$ | |
| (15) | $C(CH_3)_2$—CO—N(n-$C_4H_9$)$_2$ | |
| (16), (17) | $C(CH_3)_2$—CO—O—$C_2H_5$/$C(CH_3)_2$—CO—N(n-$C_4H_9$)$_2$ | |
| (18) | $CH(CH_3)$—CO—O—$C_8H_{17}$-i | |

Example 1

2,4,6-tris(4-[1-ethoxycarbonyl-1-methylethoxy]-2-hydroxyphenyl)-1,3,5-trazine (Compound 1)

A mixture of 203 g (0.50 mol) of 2,4,6-tris(2,4-dihydroxyphenyl)-1,3,5-triazine, 644 g (3.30 mol) of ethyl α-bromoisobutyrate (Fluka, 97%) and 112 g (1.65 mol) of sodium ethoxide (Fluka, >95%) in 1.00 l of anhydrous ethanol (Fluka, >99.8%, absolute) is heated to 78° C. under nitrogen and with stirring. After intervals of 1.5 h, 3.5 h and 4.5 h 37.4 g (0.55 mol) of sodium ethoxide (Fluka, >95%) are added to this reaction mixture. After 6 h it is cooled to 25° C. and poured into 1.00 l of 2% hydrochloric acid. The aqueous phase is extracted with ethyl acetate and the organic phase is dried over magnesium sulfate. The solvent is removed in vacuo and the title product is obtained following crystallization from isopropanol, as a pale yellow powder (melting point 150° C.).

Example 2
2,4,6-tris(4-[1-methoxycarbonyl-1-methylethoxy]-2-hydroxyphenyl)-1,3,5-triazine (Compound 2).

A mixture of 40.5 g (0.100 mol) of 2,4,6-tris(2,4-dihydroxyphenyl)-1,3,5-triazine, 119 g (0.660 mol) of methyl α-bromoisobutyrate (Fluka, 97%) and 17.8 g (0.330 mol) of sodium methoxide (Fluka, >95%) in 1.00 l of anhydrous methanol (Fluka, >99.8%, absolute) is heated to 78° C. under nitrogen and with stirring. After 2 h 17.8 g (0.330 mol) of sodium methoxide (Fluka, >95%) are added to this reaction mixture. After 16 h it is cooled to 25° C. and poured into 1.00 l of 2% hydrochloric acid. The aqueous phase is extracted with ethyl acetate and the organic phase is dried over magnesium sulfate. The solvent is removed in vacuo and the title product is obtained after column chromatography on silica gel (Fluka, size 60 silica gel, 0.040–0.063 mm) with 20:1 chloroform ethyvacetate, as a pale yellow powder (melting point 131° C.).

Example 3
2,4,6-tris(4-[1-n-butyloxycarbonyl-1-methylethoxy]-2-hydroxyphenyl)-1,3,5-triazine (Compound 3).

A mixture of 3.00 g (4.00 mmol) of 2,4,6-tris(4-[1-ethoxycarbonyl-1-methylethoxy]-2-hydroxyphenyl)-1,3,5-triazine (Compound 1), 5.90 g (80.0 mmol) of n-butanol and 0.60 g (2.40 mmol) of dibutyltin oxide in 20 ml of xylene is heated at boiling for 16 h. The ethanol which forms is distilled off during the reaction. At the end of the reaction the solvent is distilled off in vacuo. The resultant residue is chromatographed on silica gel (Fluka, size 60 silica gel, 0.040–0.063 mm) with 5:1 hexane/diethyl ether. Following the removal of the solvent the product is obtained as a yellow oil which crystallizes on prolonged standing; m.p. 86–91° C.

Examples 4–11

By the method described in Example 3 or in analogy to the transesterification technique described in GB-A-2273498 the compounds 4–11 are obtained from compound 1 and the following starting materials:

| No. | Starting material | Melting point of product |
|---|---|---|
| 4 | HO—$(CH_2)_7CH_3$ | 48–49° C. |
| 5 | HO—$(CH_2)_5CH_3$ | 71–73° C. |
| 6 | HO—$(CH_2)_6CH_3$ | 56–57° C. |
| 7 | HO—$(CH_2)_{11}CH_3$ | 53–54° C. |
| 8 | HO—$(CH_2CH_2O)CH_3$ | 98–101° C. |
| 9 | HO—$(CH_2CH_2O)_2C_2H_5$ | 47–48° C. |
| 10 | HO—$(CH_2CH_2O)_3C_2H_5$ | 42–44° C. |
| 11 | HO—$C_8H_{17}$ (isomer mixture) | 55–56° C. |

Examples 12–14

2,4,6-tris(4-[1-(N-hexylaminocarbonyl)-1-methylethoxy]-2-hydroxyphenyl)-1,3,5-triazine (Compound 12)

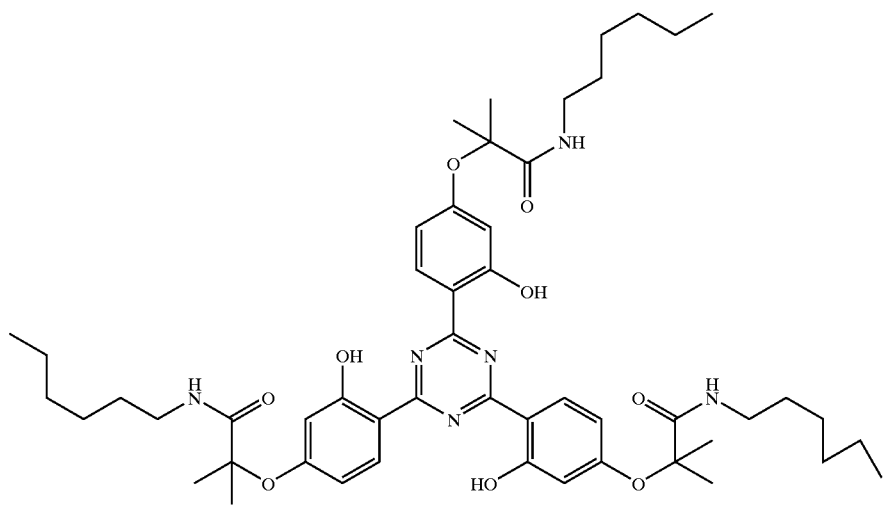

A mixture of 10.5 g (0.014 mol) of 2,4,6-tris(4-[1-ethoxycarbonyl-1-methylethoxy]-2-hydroxyphenyl)-1,3,5-triazine (Compound 1), 28.3 g (0.28 mol) of hexylamine and 2.1 g (0.0085 mol) of dibutyltin oxide in 60 ml of anhydrous xylene is heated at 130° C. under argon for 5 days. The solvent is removed in vacuo. Column chromatography gives the title product (Compound 12; $^1$H NMR(CDCl$_3$): 0.82 (m, 9H), 1.25 (m, 18H), 1.49–1.60 (m, 9H), 1.65 (s, 27H), 3.30 (d, t, J=7.5 Hz, J=6 Hz, 6H), 6.38 (t, J=6.0, 3H), 6.57–6.60 (m, 6H), 8.05 (d, J=8.6 Hz, 3H), 13.16 (s, 3H)) and also 2,4-bis(4-[1-ethoxycarbonyl-1-methylethoxy]-2-hydroxyphenyl)-6-mono-(4-[1-(N-hexylaminocarbonyl)-1-methylethoxy]-2-hydroxyphenyl)-1,3,5-triazine (Compound 13; $^1$H NMR(CDCl$_3$): 0.82 (m, 3H), 1.24–1.29 (m, 12H), 1.65 (s, 9H), 1.70 (s, 9H), 3.30 (q, J=6.7 Hz, 2H), 4.27 (q, J=7.1, 4H), 6.41–6.57 (m, 7H), 8.00 (d, J=9.6 Hz, 2H), 8.02 (d, J=9.0 Hz, 1H), 13.16 (s, 3H)), and 2-mono(4-[1-ethoxycarbonyl-1-methylethoxy]-2-hydroxyphenyl)-4,6-bis-(4-[1-(N-hexylaminocarbonyl)-1-methylethoxy]-2-hydroxyphenyl)-1,3,5-triazine (Compound 14).

Examples 15–17

2,4,6-tris(4-[1-(N,N-bis-butylaminocarbonyl)-1-methylethoxy]-2-hydroxyphenyl)-1,3,5-triazine (Compound 15)

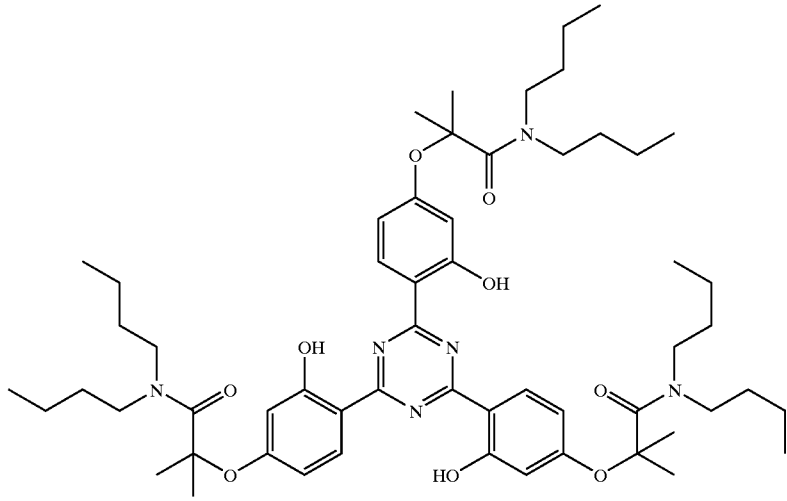

21 ml of a 2.0 M solution of trimethylaluminium in hexane are added under argon to 5.5 g (0.042 mol) of dibutylamine in 35 ml of anhydrous dichloromethane. After 15 minutes, 10.5 g (0.014 mol) of 2,4,6-tris(4-[1-ethoxycarbonyl-1-methylethoxy]-2-hydroxyphenyl)-1,3,5-triazine (Compound 1) are added to the reaction mixture. After 1 day 10 ml of anhydrous xylene are added and the dichloromethane is distilled off. The reaction mixture is subsequently heated at 130° C. for 2 days and then 10 ml of 20% HCl are added. The reaction mixture is extracted with ethyl acetate and the organic phase is dried over magnesium sulfate. The title product is obtained after column chromatography (Compound 15: $^1$H NMR(CDCl$_3$): 0.80 (t, J=7.1 Hz, 9H), 0.90 (t, J=7.1 Hz, 9H), 1.12–1.4 (m, 24H), 1.71 (s, 27H), 3.29–3.35 (m, 6H), 3.50–3.55 (m, 6H), 6.39–4.60 (m, 6H), 8.00–8.02 (m, 3H), 13.24 (s, 3H)) and also 2,4-bis(4-[1-ethoxycarbonyl-1-methylethoxy]-2-hydroxyphenyl)-6-mono-(4-[1-(N,N-bis-butylaminocarbonyl)-1-methylethoxy]-2-hydroxyphenyl)-1,3,5-triazine (Compound 16; $^1$H NMR(CDCl$_3$): 0.80–1.00 (m, 6H), 1.20–1.35 (m, 14H), 1.70 (s, 18H), 1.71 (s, 9H), 3.29–3.35 (m, 2H), 3.49–3.54 (m, 2H), 4.27 (q, J=7.1 Hz, 4H), 6.42–6.55 (m, 6H), 8.00 (d, J=9.8 Hz, 1H), 8.02 (d, J=9.00 Hz, 2H), 13.26 (s, 3H)) and 2-mono(4-[1-ethoxycarbonyl-1-methylethoxy]-2-hydroxyphenyl)-4,6-bis-(4-[1 N,N-bis-butylaminocarbonyl)-1-methylethoxy]-2-hydroxyphenyl)-1,3,5-triazine (Compound 17).

Example 18

2,4,6-tris(4-[1-octyloxycarbonyl-ethoxy]-2-hydroxyphenyl)-1,3,5-triazine (Compound 18)

A mixture of 203 g (0.50 mol) 2,4,6-tris(2,4-dihydroxyphenyl)-1,3,5-triazine is reacted with 3.30 mol of ethyl α-bromopropionate (Fluka, 97%) by the method of Example 1. The resultant trisethyl ester is transesterified with octanol (isomer mixture) in the presence of dibutyltin oxide by the method of Example 3. Following the removal of the solvent the title product (Compound 18) is obtained as a yellow oil which crystallizes on prolonged standing.

Example 19

2,4,6-Tris(2-hydroxy-4-(1-ethoxycarbonylpropoxy)phenyl)-1,3,5-triazine 10.1 g (0.025 mol) of 2,4,6-tris(2,4-dihydroxyphenyl)-1,3,5-triazine are added to a solution of 5.6 g (0.0825 mol) of sodium ethylate in 70 ml of absolute ethanol, which mixture then turns red. After heating the mixture to reflux temperature, 16.1 g (0.0825 mol) of ethyl 2-bromobutyrate are added dropwise. After 4 hours, the mixture is filtered hot, the solvent is removed by evaporation and the residue is taken up in 350 ml of ethyl acetate. After washing the organic phase with water, aqueous HCl solution and then again with water, it is dried using MgSO$_4$ and the solvent is removed by evaporation. The residue is chromatographed with hexane/ethyl acetate over silica gel, giving a compound of the following structure (m.p. 101–105° C.):

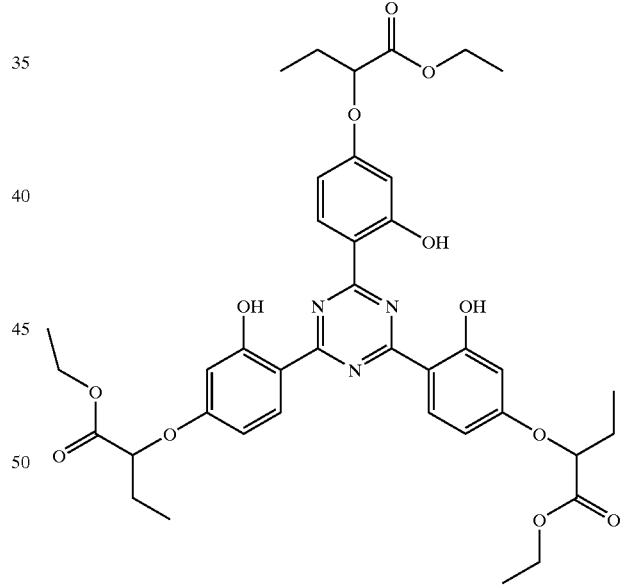

Example 20

2,4,6-Tris(2-hydroxy-4-(1-octyloxycarbonylpropoxy)phenyl)-1,3,5-triazine 10.1 g (0.025 mol) of 2,4,6-tris(2-hydroxy4-(1-ethoxycarbonylpropoxy)phenyl)-1,3,5-triazine are refluxed for 10 h with 1 g (0.004 mol) of dibutyltin oxide and 15.8 ml (0.1 mol) of octanol (isomer mixture) in 50 ml of xylene until ethanol is no longer split off. The reaction mixture is then cooled, washed with water and dried using MgSO$_4$. The solvent is concentrated and the residue is chromatographed over silica gel, giving a yellowish resinous substance of the following structure:

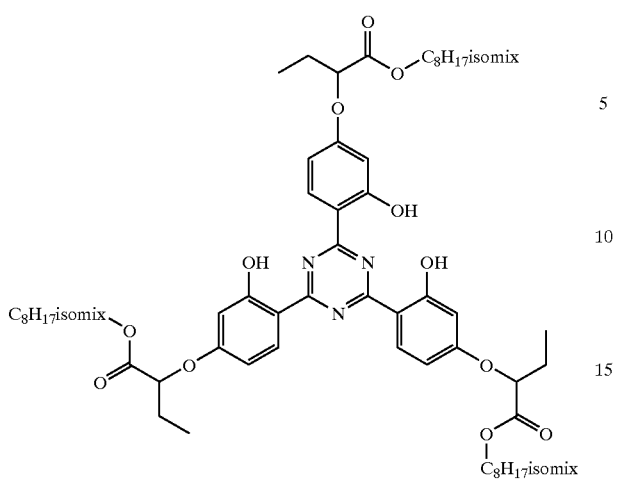

Example 21
2,4,6-Tris(2-hydroxy-4-(1-ethoxycarbonylethoxy) phenyl)-1,3,5-triazine 40.5 g (0.100 mol) of 2,4,6-tris(2,4-dihydroxyphenyl)-1,3,5-triazine and 42.8 g (0.310 mol) of anhydrous K$_2$CO$_3$ are suspended at 50° C. in 250 ml of dimethylformamide. After 30 minutes, 45.1 g (0.330 mol) of ethyl 2-chloropropionate are added and the mixture is stirred for another 14 h. The reaction mixture is filtered hot and the solvent is removed under vacuum. The residue is dissolved in 300 ml of dichloromethane and washed with water, aqueous HCl and again with water, dried using MgSO$_4$ and concentrated by evaporation. The residue is chromatographed over silica gel, giving a product of the following structure (m.p. 115–120° C.):

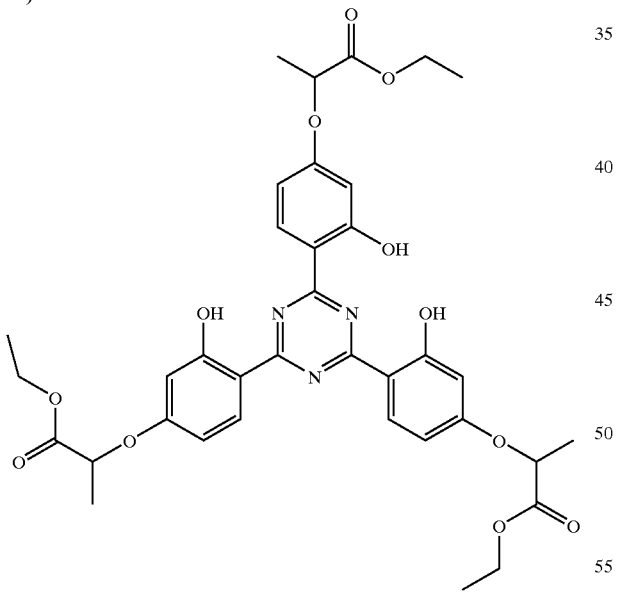

Example 22
2,4,6-Tris(2-hydroxy-4-(1-methoxycarbonylethoxy) phenyl)-1,3,5-triazine The methyl ester is prepared in analogy to the procedure of Example 21 (m.p. 145–147° C.).

Example 23
2,4,6-Tris(2-hydroxy-4-(1-octyloxycarbonylethoxy) phenyl)-1,3,5-triazine 15.60 g (0.0235 mol) of 2,4,6-tris(2-hydroxy-4-(1-methoxycarbonylethoxy)phenyl)-1,3,5-triazine are refluxed for 10 h with 0.45 g (0.00235 mol) of p-toluenesulfonic acid monohydrate and 14.85 ml (0.094 mol) of octanol (isomer mixture) in 50 ml of xylene until methanol is no longer split off. The reaction mixture is then cooled, washed with water and dried using MgSO$_4$. The solvent is concentrated and the residue is chromatographed over silica gel, giving a yellowish resinous substance of the following structure:

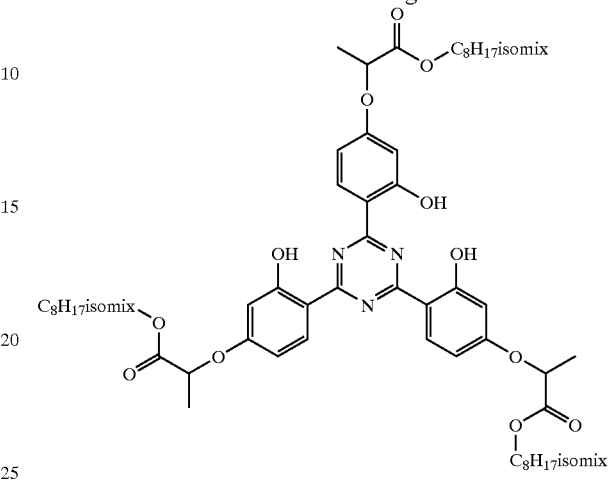

Example 24

Mixture comprising A (2,4,6-tris(2-hydroxy-4-(1-octyloxycarbonylethoxy)phenyl)-1,3,5-triazine) and B (2-(2,4-bis(1-octyloxycarbonylethoxy)phenyl)-4,6bis(2-hydroxy-4-(1-octyloxycarbonylethoxy) phenyl)-1,3,5-triazine) at a ratio of 100:1 to 1:100.

40.5 g (0.100 mol) of 2,4,6-tris(2,4-dihydroxyphenyl)-1,3,5-triazine and 48.37 g (0.350 mol) of anhydrous K$_2$CO$_3$ are suspended at 50° C. in 250 ml of dimethylformamide. After 30 minutes, 88.61 g (0.350 mol) of octyl 2-bromopropionate (octyl isomer mixture) are added and the mixture is stirred for another 14 h. The reaction mixture is filtered hot and the solvent is removed under vacuum. The residue is dissolved in 300 ml of toluene, washed with water, aqueous HCl and again with water, dried using MgSO$_4$ and concentrated by evaporation. This gives a resinous product which comprises A (as in Example 23) and B.

A

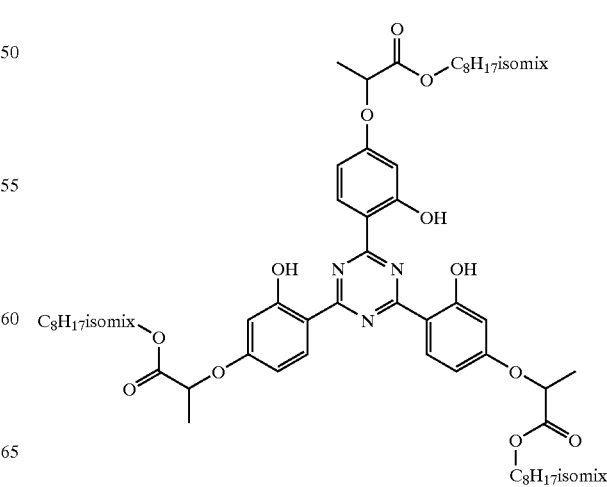

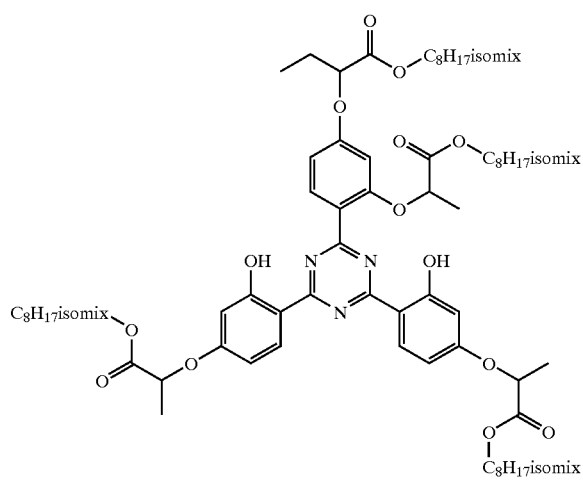

B) Use Examples

Example B1 a) Impregnation: Relative to the weight of the total formulation 0.5% of the additives indicated in Table 1 below is added to a commercially available impregnant (Xylamon Incolore™; Manufacturer: Sepam).

The impregnant is applied by brush to spruce boards (one application) and dried at room temperature for 24 hours.

b) Topcoat: A topcoat is prepared from:
- 53.48 parts by weight of alkyd resin (Jägalyd Antihydro™, E. Jäger KG, 60% solution in white spirit);
- 10.69 parts by weight of a thixotropic auxiliary (Jägalyd Antihydro-Thix™, E. Jäger KG, 50% solution);
- 1.92 parts by weight of accelerator (Jäger Antihydro-Trockner™);
- 33.44 parts by weight of solvent (Terlitol™ 30);
- 0.32 part by weight of anti-skinning agent (Ascinin™ P, BAYER);
- 0.15 part by weight of anti-skinning agent (Luactin™ M, BASF).

The topcoat is stabilized by adding 1.0% of novel UV absorber of the formula I and 1.0% of the compound of formula (hindered amine-type light stabilizer, Ciba Specialty Chemicals), the amounts being based in each case on the solids content of the binder. A comparative specimen is prepared without the addition of these stabilizers.

The topcoat is applied by brush (3 applications) to the impregnated spruce boards, which are dried at room temperature for 24 hours after each application.

The specimens are subsequently subjected to accelerated weathering: UV-A lamps with maximum light intensity at 340 nm; weathering cycle: 5 h of light at 58° C., 1 h of spraying at 22° C.

After the stated period of weathering the colour change ΔE is determined in accordance with DIN 6174; the comparison used is an unweathered specimen with unstabilized impregnant and unstabilized topcoat. The results are collated in Table 1.

TABLE 1

| Colour change ΔE in accordance with DIN 6174 on spruce, 1000 h of weathering | |
|---|---|
| Stabilizer | Colour change ΔE |
| None | 28.3 |
| Compound No. 4 | 22.1 |
| Compound No. 1 | 18.3 |

Example B2

Further specimens are prepared as in Example B1 but using pine wood and a different impregnant (Xylophene Multiusages™, Xylochimie) and applying this impregnant twice, in each case followed by drying at room temperature for 24 hours. Accelerated weathering is carried out with a Xenon Weather-o-meter™ (CAM cycle: 102 minutes of exposure at 60° C., 18 minutes of exposure/irrigation at 40° C.).

The colour change ΔE as per DIN 6174 obtained after 200 h of weathering is shown in Table 2.

TABLE 2

| Colour change ΔE in accordance with DIN 6174 on pine, 200 h of weathering. | |
|---|---|
| Stabilizer | Colour change ΔE |
| None | 8.0 |
| Compound No. 11 | 4.3 |

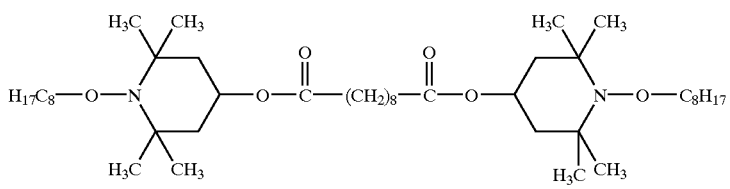

Example B3

Stabilization of a 2-coat Metallic Paint

The test compound is incorporated into 30 g of Solvesso® 100[4)] and tested in a clearcoat of the following composition (parts by weight):

| | |
|---|---|
| Synthacryl ® SC 303[1)] | 27.51 |
| Synthacryl ® SC 370[2)] | 23.34 |
| Maprenal ® 650[3)] | 27.29 |
| Butylacetate/butanol (37/8) | 4.33 |
| Isobutanol | 4.87 |
| Solvesso ® 150[4)] | 2.72 |
| Kristallöl K-30[5)] | 8.74 |
| Levelling assistant Baysilon ® MA[6)] | 1.2 |
| | 100.00 |

[1)]Acrylate resin from Hoechst AG; 65% solution in xylene/butanol (26/9)
[2)]Acrylate resin from Hoechst AG; 75% solution in Solvesso ® 100[4)]
[3)]Melamine resin from Hoechst AG; 55% solution in isobutanol
[4)]Mixture of aromatic hydrocarbons (Manufacturer: Esso); boiling range 182–203° C. (Solvesso ® 150) or 161–178° C. (Solvesso ® 100)
[5)]Mixture of aliphatic hydrocarbons (Manufacturer: Shell); boiling range 145–200° C.
[6)]1% in Solvesso ® 150[4)] (Manufacturer: Bayer AG)

1.5% by weight of compound No. 11 is added to the clearcoat; in some samples, an additional 0.7% of the compound

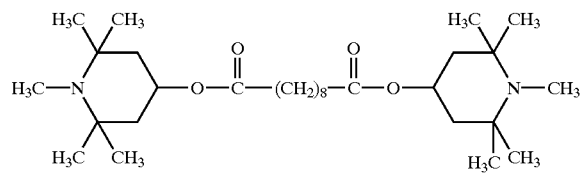

(Compound A) is incorporated (amounts based in each case on the solids content of the coating material). The comparison material used is a clearcoat containing no light stabilizer.

The clearcoat is diluted to spray viscosity with Solvesso® 100 and applied by spraying to a prepared aluminium panel (Uniprime® Epoxy, silver metallic basecoat) and the painted panel is baked at 130° C. for 30 minutes. The result is a clearcoat dry-film thickness of 40–50 μm.

The samples are then weathered in an UVCON® weathering device from Atlas Corp. (UVB-313 lamps) with a cycle of 4 h of UV irradiation at 70° C. and 4 h condensation at 50° C.

The samples are examined at regular intervals for gloss (20° gloss as per DIN 67530) and freedom from cracks.

The samples that are stabilized in accordance with the invention exhibit much better weathering stability (gloss retention, freedom from cracks) than the unstabilized comparative sample.

Example B4

The procedure of Example B3 is repeated but with the clearcoat containing, rather than 0.7% of compound A, 1.0% by weight of a compound of the formula

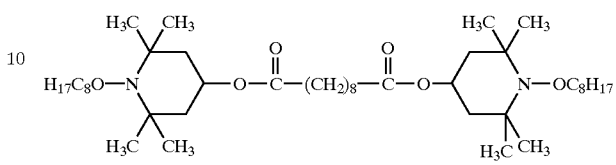

(Compound B) and with the paint being applied to a red metallic basecoat. The amount of novel stabilizer of the formula I employed is indicated in Table 4 below (identified by the compound number; amounts based in each case on the solids content of the coating material).

The samples are examined at regular intervals for gloss (20° gloss as per DIN 67530) and freedom from cracking; before the beginning of weathering a gloss value of 94 is measured. The results are collated in Table 4 below.

TABLE 4

| 20° gloss as per DIN 67530 after 2400 h of weathering | | |
|---|---|---|
| Stabilizers Compd. B | Formula I | 20° gloss |
| none | none | — (crack after 1600 h) |
| 1% B | none | 44 |
| 1% B | 1% Compd. 1 | 87 |
| 1% B | 1% Compd. 4 | 86 |

The samples that are stabilized in accordance with the invention exhibit excellent gloss retention and freedom from cracking.

Example B5

Wood Varnish

A topcoat is prepared from:

| | |
|---|---|
| 73.80 | parts by weight of alkyl resin (Jagol PS 21 ™, E. JÄGER KG, 100%); |
| 4.16 | parts by weight of accelerator (Jäger Antihydro-Trockner ™); |
| 20.80 | parts by weight of solvent (Exxol ™ D 40, EXXON); |
| 0.52 | part by weight of anti-skinning agent (Exkin 2 ™, EXXON); |
| 0.72 | part by weight of anti-skinning agent (Lanco Glidd AH ™; Lubrizol Coatings Additives, Germany). |

Application takes place as described in Example B2; the amount of stabilizer of the invention is 1% based on the weight of the solids content of the varnish. Compound 11 is incorporated as an 85% by weight solution in methoxypropanol.

Accelerated weathering takes place by means of a Xenon Weather-o-meter™ (CAM 7 cycle).

The colour change ΔE as per DIN 6174 after 800 h of weathering is shown in Table 5.

TABLE 5

| Colour change ΔE in accordance with DIN 6174 on pine, 800 h of weathering | |
|---|---|
| Stabilizer | Colour change ΔE |
| None | 22.3 |
| Compound No. 11 | 11.7 |
| Compound No. 18 | 11.6 |

Example B6

Incorporation into a Photographic Material

A gelatin layer having the following composition (per m$^2$) is applied conventionally to a polyester base:

| Component: | Amount: |
|---|---|
| Gelatin | 1200 mg |
| Tricresyl phosphate | 510 mg |
| Curing agent | 40 mg |
| Wetting agent | 100 mg |
| Compound of formula I | 225 mg |

The curing agent is the potassium salt of 2-hydroxy-4,6dichloro-1,3,5-triazine. The wetting agent is sodium 4,8-diisobutyinaphthalene-2-sulfonate.

The gelatin layers are dried for 7 days at 20° C.

When the novel Compound No. 11 is used, clear transparent layers are obtained which are suitable for a photographic recording material, for example as a UV filter layer.

What is claimed is:
1. A composition comprising

A) an organic material sensitive to damage by light, oxygen and/or heat, and

B) as stabilizer, a compound of the formula I

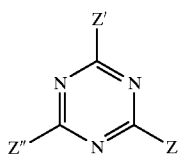
(I)

in which Z, Z' and Z" independently of one another are a group of the formula II

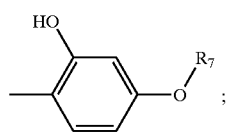
(II)

$R_7$ is a radical of the formula III, IV or V

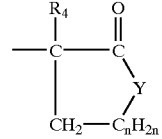
(III)

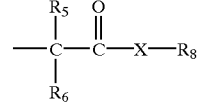
(IV)

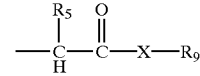
(V)

in which n is 1 or 2;
$R_4$, $R_5$ and $R_6$ independently of one another are $C_1$–$C_{18}$alkyl; $C_5$–$C_{12}$cycloalkyl; $C_2$–$C_{18}$alkenyl; phenyl; $C_7$–$C_{11}$phenylalkyl; $C_7$–$C_{11}$alkylphenyl; $C_1$–$C_{18}$alkyl substituted by phenyl, OH, halogen; $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkyl-alkoxy, $C_6$–$C_{16}$bicycloalkenyl-alkoxy or $C_6$–$C_{15}$tricycloalkoxy; $C_5$–$C_{12}$cycloalkyl substituted by OH, $C_1$–$C_4$alkyl, $C_2$–$C_6$alkenyl or O—COR$_{12}$; or COR$_{15}$; CO—X—R$_8$; or SO$_2$—R$_{16}$; or $C_3$–$C_{50}$alkyl interrupted by O and/or substituted by OH, phenoxy, or $C_7$–$C_{18}$alkylphenoxy;
or $R_5$ and $R_6$, together with the carbon atom to which they are attached, form a $C_4$–$C_8$cycloalkyl ring which is uninterrupted or interrupted by O, NH, NR$_{13}$, or S and/or unsubstituted or substituted by $C_1$–$C_6$alkyl, $C_1$–$C_6$alkoxy, OH, phenoxy or $C_7$–$C_{18}$alkylphenoxy;
$R_8$ is H or as defined for $R_{11}$;
$R_9$ is $C_3$–$C_{18}$alkyl; $C_3$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; $C_6$–$C_{15}$bicycloalkyl; $C_6$–$C_{15}$bicycloalkenyl; $C_6$–$C_{16}$tricycloalkyl; or $C_1$–$C_{18}$alkyl substituted by halogen, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{15}$bicycloalkenyl;
$R_{11}$ is $C_1$–$C_{18}$alkyl; $C_5$–$C_{12}$cycloalkyl; $C_6$–$C_{14}$aryl; $C_2$–$C_{18}$alkenyl; $C_7$–$C_{14}$alkylphenyl; $C_1$–$C_{18}$alkyl substituted by phenyl, phenoxy, naphthyl, naphthyloxy, OH, halogen, $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkyl-alkoxy, $C_6$–$C_{16}$bicycloalkenyl-alkoxy or $C_6$–$C_{15}$tricycloalkoxy or by a phenyl, phenyloxy or naphthyloxy, which itself is substituted by halogen, OH, $C_1$–$C_4$alkyl, $C_1$–$C_4$alkoxy, $C_1$–$C_8$alkylamino, cyclohexylamino, $C_1$–$C_8$alkylthio, cyclohexylthio; or $R_{11}$ is $C_5$–$C_{12}$cycloalkyl substituted by OH, $C_1$–$C_4$alkyl, $C_2$–$C_6$alkenyl or O—$COR_{12}$; or is $COR_{15}$; or $SO_2$—$R_{16}$; or a carbon-linked 5–7 membered heterocyclic residue containing 4–12 carbon and 1–3 heteroatoms selected from O, N and S; or $R_{11}$ is $C_3$–$C_{50}$alkyl interrupted by O, NH, $NR_{13}$, S and/or substituted by OH, phenoxy, $C_3$–$C_{18}$alkenoxy, $C_7$–$C_{18}$alkylphenoxy, O—$COR_{12}$, O—P(=O)($OR_{12}$)$_2$, O—P(=O)($R_{12}$)$_2$, O—Si($OR_{12}$)$_3$;

$R_{12}$ is $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; $C_6$–$C_{15}$bicycloalkyl; $C_6$–$C_{15}$bicycloalkenyl; $C_6$–$C_{15}$tricycloalkyl;

$R_{13}$ and $R_{14}$ independently of one another are $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; or $C_3$–$C_{30}$alkyl interrupted by O, NH or $NR_{13}$ and/or substituted by OH; or are $C_6$–$C_{15}$bicycloalkyl; $C_6$–$C_{15}$bicycloalkenyl; or $C_6$–$C_{15}$tricycloalkyl;

$R_{15}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{16}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{17}$ is $CH_2$—O—$R_{15}$ or furfuryl or tetrahydrofurfuryl or is $C_3$–$C_{30}$alkyl interrupted by O, NH, $NR_{13}$ and/or substituted by OH; and X and Y independently of one another are O, NH, $NR_{13}$ or S, with the exception of the compound 2,4,6-tris(2-hydroxy4-[1-ethyloxycarbonyl-1-methylethoxy]phenyl)-1,3,5-triazine.

2. A composition according to claim 1, comprising from 0.01 to 15% parts by weight of component B per 100 parts by weight of component A.

3. A composition according to claim, 1, in which component A is a thermpolastic polymer or a binder for a surface coating or a photographic material.

4. A composition according to claim 1, in which component A is a synthetic organic polymer or prepolymer or a photographic material and. component B is a compound of the formula I

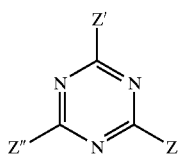
(I)

in which Z, Z' and Z" independently of one another are a group of the formula II

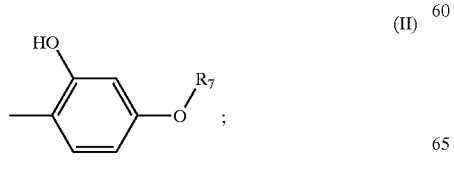
(II)

$R_7$ is a radical of the formula III, IV or V

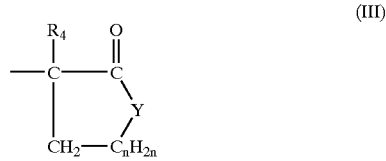
(III)

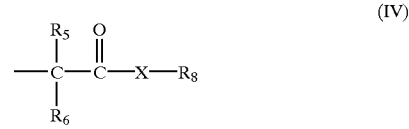
(IV)

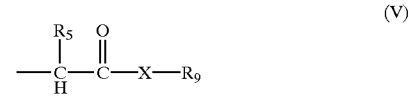
(V)

in which n is 1 or 2;

$R_4$, $R_5$ and $R_6$ independently of one another are $C_1$–$C_{18}$alkyl; $C_5$–$C_{12}$cycloalkyl; $C_2$–$C_{18}$alkenyl; phenyl; $C_7$–$C_{11}$phenylalkyl; $C_7$–$C_{11}$alkylphenyl; $C_1$–$C_{18}$alkyl substituted by phenyl, OH, halogen; $C_1$–$C_{18}$alkoxy, $C_5$–$C_{12}$cycloalkoxy, $C_3$–$C_{18}$alkenyloxy, COOH, $COOR_{11}$, O—$COR_{12}$, $CONH_2$, $CONHR_{13}$, $CONR_{13}R_{14}$, CN, $NH_2$, $NHR_{13}$, $NR_{13}R_{14}$, $NHCOR_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkylalkoxy, $C_6$–$C_{16}$bicycloalkenyl-alkoxy or $C_6$–$C_{15}$tricycloalkoxy; $C_5$–$C_{12}$cycloalkyl substituted by OH, $C_1$–$C_4$alkyl, $C_2$–$C_6$alkenyl or O—$COR_{12}$; or $COR_{15}$; CO—X—$R_8$; or $SO_2$—$R_{16}$; or $C_3$–$C_{50}$alkyl interrupted by O and/or substituted by OH, phenoxy, or $C_7$–$C_{18}$alkylphenoxy; or $R_5$ and $R_6$, together with the carbon atom to which they are attached, form a $C_4$–$C_8$cycloalkyl ring which is uninterrupted or interrupted by O, NH, $NR_{13}$, or S and/or unsubstituted or substituted by $C_1$–$C_6$alkyl, $C_1$–$C_6$alkoxy, OH, phenoxy or $C_7$–$C_{18}$alkylphenoxy;

$R_8$ is H or as defined for $R_{11}$;

$R_9$ is $C_1$–$C_{18}$alkyl; $C_3$–$C_{18}$alkenyl; $C_5$–$C_{12}$cycloalkyl; $C_1$–$C_4$alkylcyclohexyl; $C_6$–$C_{14}$aryl; $C_7$–$C_{14}$alkylphenyl; $C6$–$C_{15}$bicycloalkyl; $C_6$–$C_{15}$bicycloalkenyl; $C_6$–$C_{16}$tricycloalkyl; or $C_1$–$C_{18}$alkyl substituted by halogen, COOH, $COOR_{11}$, O—$COR_{12}$, $CONH_2$, $CONHR_{13}$, $CONR_{13}R_{14}$, CN, $NH_2$, $NHR_{13}$, $NR_{13}R_{14}$, $NHCOR_{12}$, $C_6$–$C_{15}$bicycloalkyl, $C_6$–$C_{15}$bicycloalkenyl; especially $C_6$–$C_{12}$alkyl;

$R_{11}$ is $C_1$–$C_{18}$alkyl; $C_5$–$C_{12}$cycloalkyl; $C_6$–$C_{14}$aryl; $C_2$–$C_{18}$alkenyl; $C_7$–$C_{14}$alkylphenyl; $C_1$–$C_{18}$alkyl substituted by phenyl, phenoxy, naphthyl, naphthyloxy, OH, halogen, $C_1$–$C_{18}$alkoxy, $C_5$–$C_{12}$cycloalkoxy, $C_3$–$C_{18}$alkenyloxy, COOH, $COOR_{11}$, O—$COR_{12}$, $CONH_2$, $CONHR_{13}$, $CONR_{13}R_{14}$, CN, $NH_2$, $NHR_{13}$, $NR_{13}R_{14}$, $NHCOR_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkylalkoxy, $C_6$–$C_{16}$bicycloalkenyl-alkoxy or $C_6$–$C_{15}$tricycloalkoxy or by a phenyl, phenyloxy or naphthyloxy, which itself is substituted by halogen, OH, $C_1$–$C_4$alkyl, $C_1$–$C_4$alkoxy, $C_1$–$C_8$alkylamino, cyclohexylamino, $C_1$–$C_8$alkylthio, cyclohexylthio; or $R_{11}$ is $C_5$–$C_{12}$cycloalkyl substituted by OH, $C_1$–$C_4$alkyl, $C_2$–$C_6$alkenyl or O—$COR_{12}$; or is COR$_{15}$; or SO$_2$—R$_{16}$; or a carbon-linked, 5–7 membered heterocyclic residue containing 4–12 carbon and 1–3 heteroatoms selected from O, N and S; or R$_{11}$ is C$_3$–C$_{50}$alkyl interrupted by O, NH, NR$_{13}$, S and/or substituted by OH, phenoxy, C$_3$–C$_{18}$alkenoxy, C$_7$–C$_{18}$alkylphenoxy, O—COR$_{12}$, O—P(=O)(OR$_{12}$)$_2$, O—P(=O)(R$_{12}$)$_2$, O—Si(OR$_{12}$)$_3$;

R$_{12}$ is C$_1$–C$_{18}$alkyl; C$_2$–C$_{18}$alkenyl; C$_5$–C$_{12}$cycloalkyl; C$_1$–C$_4$alkylcyclohexyl; C$_6$–C$_{14}$aryl; C$_7$–C$_{11}$phenylalkyl; C$_7$–C$_{14}$alkylphenyl; C$_6$–C$_{15}$bicycloalkyl; C$_6$–C$_{15}$bicycloalkenyl; C$_6$–C$_{15}$tricycloalkyl;

R$_{13}$ and R$_{14}$ independently of one another are C$_1$–C$_{18}$alkyl; C$_2$–C$_{18}$alkenyl; C$_5$–C$_{12}$cycloalkyl; C$_1$–C$_4$alkylcyclohexyl; C$_6$–C$_{14}$aryl; C$_7$–C$_{11}$phenylalkyl; C$_7$–C$_{14}$alkylphenyl; or C$_3$–C$_{30}$alkyl interrupted by O, NH or NR$_{13}$ and/or substituted by OH; or are C$_6$–C$_{15}$bicycloalkyl; C$_6$–C$_{15}$bicycloalkenyl; or C$_6$–C$_{15}$tricycloalkyl;

R$_{15}$ is C$_1$–C$_{18}$alkyl; C$_2$–C$_{18}$alkenyl; C$_5$–C$_{12}$cycloalkyl; C$_6$–C$_{14}$aryl; C$_7$–C$_{11}$phenylalkyl; or C$_7$–C$_{14}$alkylphenyl;

R$_{16}$ is C$_1$–C$_{18}$alkyl; C$_2$–C$_{18}$alkenyl; C$_5$–C$_{12}$cycloalkyl; C$_6$–C$_{14}$aryl; C$_7$–C$_{11}$phenylalkyl; or C$_7$–C$_{14}$alkylphenyl;

R$_{17}$ is CH$_2$—O—R$_{15}$ or furfuryl or tetrahydrofurfuryl or is C$_3$–C$_{30}$alkyl interrupted by O, NH, NR$_{13}$ and/or substituted by OH; and X and Y independently of one another are O, NH, NR$_{13}$ or S;

with the exception of a composition wherein component A is a photographic material additionally comprising a compound of the formula XV

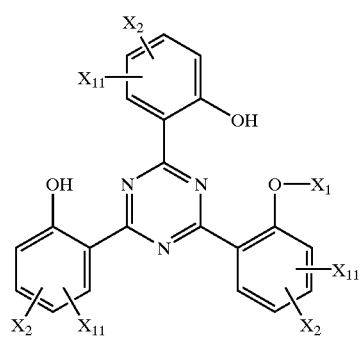

(XV)

in which X$_1$ is a hydrocarbon radical with or without heteroatoms and X$_2$ and X$_{11}$ independently of one another are hydrogen or a hydrocarbon radical with or without a heteroatom.

5. A composition according to claim 4, in which component A is a thermoplastic polymer or a binder for coatings or a color photographic material.

6. A composition according to claim 4, in which component B is a compound of the formula I, wherein R$_7$ is a radical of the formula III, IV or V and R$_4$, R$_5$ and R$_6$ independently of one another are C$_1$–C$_{18}$alkyl; C$_5$–C$_{12}$cycloalkyl; C$_2$–C$_{18}$alkenyl; phenyl; C$_7$–C$_{11}$phenylalkyl; C$_7$–C$_{11}$alkylphenyl; C$_1$–C$_{18}$alkyl substituted by phenyl, C$_1$–C$_{18}$alkoxy, C$_5$–C$_{12}$cycloalkoxy, C$_3$–C$_{18}$alkenyloxy or C$_6$–C$_{15}$bicycloalkyl; or COR$_{15}$; CO—X—R$_{11}$; or SO$_2$—R$_{16}$; or are C$_3$–C$_{50}$alkyl interrupted by O and/or substituted by OH, phenoxy, or C$_7$–C$_{18}$alkylphenoxy;

or R$_5$ and R$_6$, together with the carbon atom to which they are attached, form a C$_5$–C$_6$cycloalkyl ring which is uninterrupted or interrupted by O, NH, NR$_{13}$ and/or unsubstituted or substituted by C$_1$–C$_6$alkyl, OH, phenoxy or C$_7$–C$_{18}$alkylphenoxy;

R$_8$ is as defined for R$_{11}$;

R$_9$ is C$_6$–C$_{12}$alkyl, C$_6$–C$_{12}$cycloalkyl or C$_7$–C$_{12}$phenylalkyl;

R$_{11}$ is C$_1$–C$_{18}$alkyl; C$_2$–C$_{18}$alkenyl; C$_5$–C$_{12}$cycloalkyl; phenyl; C$_7$–C$_{11}$phenylalkyl; C$_7$–C$_{14}$alkylphenyl; or C$_3$–C$_{30}$alkyl interrupted by O and/or substituted by OH, phenoxy, O—COR$_{12}$, O—P(=O)(OR$_{12}$)$_2$, O—P(=O)(R$_{12}$)$_2$, O—Si(OR$_{12}$)$_3$; or is CH$_2$—CH(OH)—R$_{17}$, furfuryl or tetrahydrofurfuryl;

R$_{12}$ is C$_1$–C$_{18}$alkyl; C$_2$–C$_{18}$alkenyl; C$_5$–C$_{12}$cycloalkyl; C$_1$–C$_4$alkylcyclohexyl; C$_6$–C$_{14}$aryl; C$_7$–C$_{11}$phenylalkyl; C$_7$–C$_{14}$alkylphenyl; C$_6$–C$_{15}$bicycloalkyl; C$_6$–C$_{15}$bicycloalkenyl or C$_6$–C$_{15}$tricycloalkyl;

R$_{13}$ and R$_{14}$ independently of one another are C$_1$–C$_{18}$alkyl; allyl; C$_5$–C$_{12}$cycloalkyl; phenyl; C$_7$–C$_{11}$phenylalkyl; C$_7$–C$_{14}$alkylphenyl; or C$_3$–C$_{30}$alkyl interrupted by O and/or substituted by OH; or are C$_6$–C$_{15}$bicycloalkyl; C$_6$–C$_{15}$bicycloalkenyl; or C$_6$–C$_{15}$tricycloalkyl;

R$_{15}$ is C$_1$–C$_{18}$alkyl; C$_2$–C$_{18}$alkenyl; C$_5$–C$_{12}$cycloalkyl; C$_6$–C$_{14}$aryl; C$_7$–C$_{11}$phenylalkyl; or C$_7$–C$_{14}$alkylphenyl;

R$_{16}$ is C$_1$–C$_{18}$alkyl; C$_2$–C$_{18}$alkenyl; C$_5$–C$_{12}$cycloalkyl; C$_6$–C$_{14}$aryl; C$_7$–C$_{11}$phenylalkyl; or C$_7$–C$_{14}$alkylphenyl;

R$_{17}$ is CH$_2$—O—R$_{15}$, furfuryl or tetrahydrofurfuryl or is C$_3$–C$_{30}$alkyl interrupted by O and/or substituted by OH; and X and Y independently of one another are O, NH or NR$_{13}$.

7. A composition according to claim 1, which component A is a stain, impregnation or protective coating on wood and component B is a compound of the formula I

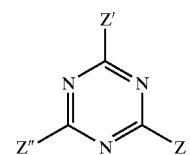

(I)

in which Z, Z' and Z" independently of one another are a group of the formula II

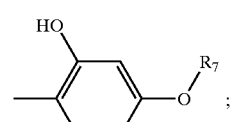

(II)

$R_7$ is a radical of the formula III, IV or V

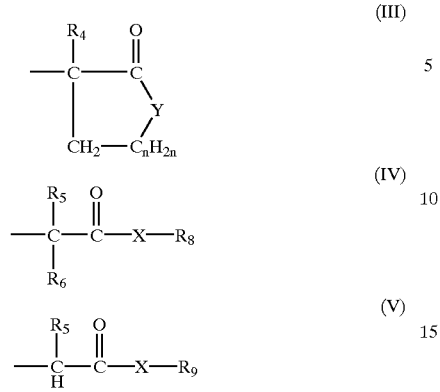

in which n is 1 or 2;

$R_4$, $R_5$ and $R_6$ independently of one another are $C_1$–$C_{18}$alkyl; $C_5$–$C_{12}$cycloalkyl; $C_2$–$C_{18}$alkenyl; phenyl; $C_7$–$C_{11}$phenylalkyl; $C_7$–$C_{11}$alkylphenyl; $C_1$–$C_{18}$alkyl substituted by phenyl, OH, halogen; $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{16}$bicycloalkyl-alkoxy, $C_6$–$C_{16}$bicycloalkenyl-alkoxy or $C_6$–$C_{15}$tricycloalkoxy; $C_5$–$C_{12}$cycloalkyl substituted by OH, $C_1$–$C_4$alkyl, $C_2$–$C_6$alkenyl or O—COR$_{12}$; or COR$_{15}$; CO—X—R$_{16}$; or SO$_2$—R$_{16}$; or $C_3$–$C_{50}$alkyl interrupted by O and/or substituted by OH, phenoxy, or $C_7$–$C_{18}$alkylphenoxy;

or $R_5$ and $R_6$, together with the carbon atom to which they are attached, form a $C_4$–$C_8$cycloalkyl ring which is uninterrupted or interrupted by O, NH, NR$_{13}$, or S and/or unsubstituted or substituted by $C_1$–$C_6$alkyl, OH, phenoxy or $C_7$–$C_{18}$alkylphenoxy;

$R_8$ and $R_9$, independently, are H or as defined for $R_{11}$;

$R_{11}$ is $C_1$–$C_{18}$alkyl; $C_5$–$C_{12}$ cycloalkyl; $C_6$–$C_{14}$aryl; $C_2$–$C_{18}$alkenyl; $C_7$–$C_{14}$alkylphenyl; $C_1$–$C_{18}$alkyl substituted by phenyl, phenoxy, naphthyloxy, OH, halogen, $C_1$–$C_{18}$alkoxy, $C_5$–$C_{12}$cycloalkoxy, $C_3$–$C_{18}$alkenyloxy, COOH, COOR$_{11}$, O—COR$_{12}$, CONH$_2$, CONHR$_{13}$, CONR$_{13}$R$_{14}$, CN, NH$_2$, NHR$_{13}$, NR$_{13}$R$_{14}$, NHCOR$_{12}$, $C_6$–$C_{15}$bicycloalkyl, $C_6$–$C_{15}$bicycloalkoxy, $C_6$–$C_{15}$bicycloalkenyl, $C_6$–$C_{15}$bicycloalkenyloxy, $C_6$–$C_{16}$bicycloalkyl-alkoxy, $C_6$–$C_{16}$bicycloalkenyl-alkoxy or $C_6$–$C_{15}$tricycloalkoxy or by a phenyl, phenyloxy or naphthyloxy, which itself is substituted by halogen, OH, $C_1$–$C_4$alkyl, $C_1$–$C_4$alkoxy, $C_1$–$C_8$alkylamino, cyclohexylamino, $C_1$–$C_8$alkylthio, cyclohexylthio; or $R_{11}$ is $C_5$–$C_{12}$cycloalkyl substituted by OH, $C_1$–$C_4$alkyl, $C_2$–$C_6$alkenyl or O—COR$_{12}$; or is COR$_{15}$; or SO$_2$—R$_{16}$; or a carbon-linked, 5–7 member heterocyclic residue containing 4–12 carbon and 1–3 heteroatoms selected from O, N and S; or $R_{11}$ is $C_3$–$C_{50}$alkyl interrupted by O, NH, NR$_{13}$, S and/or substituted by OH, phenoxy, $C_3$–$C_{18}$alkenoxy, $C_7$–$C_{18}$alkylphenoxy, O—COR$_{12}$, O—P(=O)(OR$_{12}$)$_2$, O—P(=O)(R$_{12}$)$_2$, O—Si(OR$_{12}$)$_3$;

$R_{12}$ is $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; $C_6$–$C_{15}$bicycloalkyl; $C_6$–$C_{15}$bicycloalkenyl; $C_6$–$C_{15}$tricycloalkyl;

$R_{13}$ and $R_{14}$ independently of one another are $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; or $C_3$–$C_{30}$alkyl interrupted by O, NH or NR$_{13}$ and/or substituted by OH; or are $C_6$–$C_{15}$bicycloalkyl; $C_6$–$C_{15}$bicycloalkenyl; or $C_6$–$C_{15}$tricycloalkyl;

$R_{15}$ is $C_1$–$C_{18}$alkyl; $C_2$–$C_{11}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{16}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{17}$ is CH$_2$—O—R$_{15}$ or furfuryl or tetrahydrofurfuryl or is $C_3$–$C_{30}$alkyl interrupted by O, NH, NR substituted by OH; and X and Y independently of one another are O, NH, NR$_{13}$ or S.

8. A composition according to claim 7, in which component B is a compound of the formula I, wherein $R_7$ is a radical of the formula III, IV or V and $R_4$, $R_5$ and $R_6$ independently of one another are $C_1$–$C_{18}$alkyl; $C_5$–$C_{12}$cycloalkyl; $C_2$–$C_{18}$alkyl; phenyl; $C_7$–$C_{11}$phenylalkyl; $C_7$–$C_{11}$alkylphenyl; $C_1$–$C_{18}$alkyl substituted by phenyl, $C_1$–$C_{18}$alkoxy, $C_5$–$C_{12}$cycloalkoxy, $C_3$–$C_{18}$alkenyloxy or $C_6$–$C_{15}$bicycloalkyl; or COR$_{15}$; CO—X—R$_{11}$; or SO$_2$—R$_{16}$; or are $C_{3-C50}$alkyl interrupted by O and/or substituted by OH, phenoxy, or $C_7$–$C_{18}$alkylphenoxy; or $R_5$ and $R_6$, together with the carbon atom to which they are attached, form a $C_5$–$C_6$cycloalkyl ring which is uninterrupted or interrupted by O, NH, NR$_{13}$ and/or unsubstituted or substituted by $C_1$–$C_6$alkyl, OH, phenoxy or $C_7$–$C_{18}$alkylphenoxy;

$R_8$ is as defined for $R_{11}$;

$R_9$ is $C_6$–$C_{12}$alkyl, $C_6$–$C_{12}$cycloalkyl or $C_7$–$C_{12}$phenylalkyl;

$R_{11}$ is $C_1$–$C_{18}$alkyl; $C_2$–$C_{18}$alkenyl; $C_5$–$C_{12}$cycloalkyl; phenyl; $C_7$–$C_{11}$phenylalkyl; $C_7$–$C_{14}$alkylphenyl; or $C_3$–$C_{30}$alkyl interrupted by O and/or substituted by OH, phenoxy, O—COR$_{12}$, O—P(=O)(OR$_{12}$)$_2$, O—P(=O)(R$_{12}$)$_2$, O—Si(OR$_{12}$)$_3$; or is CH$_2$—CH(OH)—R$_{17}$, furfuryl or tetrahydrofurfuryl;

$R_{12}$ is $C_1$–$C_{18}$alkyl; $C_2$–$C_{18}$alkenyl; $C_5$–$C_{12}$cycloalkyl; $C_1$–$C_4$alkylcyclohexyl; $C_6$–$C_{14}$aryl; $C_7$–$C_{11}$phenylalkyl; $C_7$–$C_{14}$alkylphenyl; $C_6$–$C_{15}$bicycloalkyl; $C_6$–$C_{15}$bicycloalkenyl or $C_6$–$C_{15}$-tricycloalkyl;

$R_{13}$ and $R_{14}$ independently of one another are $C_1$–$C_{18}$alkyl; allyl; $C_5$–$C_{12}$cycloalkyl; phenyl; $C_7$–$C_{11}$phenylalkyl; $C_7$–$C_{14}$alkylphenyl; or $C_3$–$C_{30}$alkyl interrupted by O and/or substituted by OH; or are $C_6$–$C_{15}$bicycloalkyl; $C_6$–$C_{15}$bicycloalkenyl; or $C_6$–$C_{15}$tricycloalkyl;

$R_{15}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{16}$ is $C_1$–$C_{18}$alkyl; $C_2$–$C_{18}$alkenyl; $C_5$–$C_{12}$cycloalkyl; $C_6$–$C_{14}$aryl; $C_7$–$C_{11}$phenylalkyl; or $C_7$–$C_{14}$alkylphenyl;

$R_{17}$ is CH$_2$—O—R$_{15}$, furfuryl or tetrahydrofurfuryl or is $C_3$–$C_{30}$alkyl interrupted by O and/or substituted by OH; and X and Y independently of one another are O, NH or NR$_{13}$.

9. A composition according to any of claim 1, comprising as further component one or more compounds selected from the group consisting of antioxidants, phosphites, phosphonites, benzofuranones, indolinones and light stabilizers of the type of the sterically hindered amines, of the 2-(2-hydroxyphenyl)-1,3,5-triazines, 2-hydroxyphenyl-2H-benzotriazoles, 2-hydroxybenzophenones and/or of the oxalanilides.

10. A method of stabilizing organic material against deleterious effects of light, oxygen and/or heat, which comprises admixing and/or applying to the said material as stabilizer a compound of the formula I according to claim 1.

* * * * *